(12) United States Patent
Facchetti et al.

(10) Patent No.: US 8,598,575 B2
(45) Date of Patent: Dec. 3, 2013

(54) SEMICONDUCTING COMPOUNDS AND RELATED COMPOSITIONS AND DEVICES

(71) Applicant: Polyera Corporation, Skokie, IL (US)

(72) Inventors: Antonio Facchetti, Chicago, IL (US); Zhihua Chen, Skokie, IL (US); Hakan Usta, Evanston, IL (US); Christopher Newman, Evanston, IL (US); He Yan, Hong Kong (CN)

(73) Assignee: Polyera Corporation, Skokie, IL (US)

( * ) Notice: Subject to any disclaimer, the term of this patent is extended or adjusted under 35 U.S.C. 154(b) by 0 days.

(21) Appl. No.: 13/775,211

(22) Filed: Feb. 24, 2013

(65) Prior Publication Data
US 2013/0168659 A1 Jul. 4, 2013

Related U.S. Application Data

(63) Continuation of application No. PCT/US2011/049411, filed on Aug. 26, 2011.

(60) Provisional application No. 61/377,964, filed on Aug. 29, 2010.

(51) Int. Cl.
*H01L 51/00* (2006.01)

(52) U.S. Cl.
USPC ........... 257/40; 257/288; 257/E51.05; 549/49

(58) Field of Classification Search
USPC .................................................. 257/40, 288
See application file for complete search history.

(56) References Cited

U.S. PATENT DOCUMENTS 8,039,625 B2 * 10/2011 Marder et al. .................. 546/28

FOREIGN PATENT DOCUMENTS

JP 2009123738 A * 6/2009

OTHER PUBLICATIONS

Gorodetsky et al. "Reticulated Heterojunctions for Photovoltaic Devices." Angew. Chem. Int. Ed. 49, 9709-7912, 2010.*
Thelakkat et al. "Bis(thienyl) coronene and its electrochemical polymerization." Synthetic Metals 68, 153-155, 1995.*

* cited by examiner

*Primary Examiner* — Matthew W Such
*Assistant Examiner* — Stephen Bradley
(74) *Attorney, Agent, or Firm* — Karen K. Chan

(57) ABSTRACT

Disclosed are new semiconductor materials prepared from thienocoronene-based compounds and related heteroaromatic analogs. Such compounds can exhibit high carrier mobility and/or good current modulation characteristics. In addition, the compounds of the present teachings can possess certain processing advantages such as solution-processability and/or good stability at ambient conditions.

20 Claims, 2 Drawing Sheets a)

b)

c)

d)

SEMICONDUCTING COMPOUNDS AND RELATED COMPOSITIONS AND DEVICES

CROSS-REFERENCE TO RELATED APPLICATIONS

This application is a continuation of International Application No. PCT/US2011/049411, filed on Aug. 26, 2011, which claims priority to and the benefit of U.S. Provisional Patent Application Ser. No. 61/377,964, filed on Aug. 29, 2010, the disclosure of each of which is incorporated by reference herein in its entirety.

BACKGROUND

Organic optoelectronic devices such as organic thin film transistors (OTFTs), organic light emitting diodes (OLEDs), printable circuits, organic photovoltaic devices, capacitors and sensors are fabricated using small molecule or polymeric semiconductors as their active components. To achieve high speed performance and efficient operation, it is desirable that both the p-type and n-type semiconductor materials in these organic semiconductor-based devices exhibit high charge carrier mobility ($\mu$) and stability under ambient conditions, and can be processed in a cost-effective manner.

Accordingly, the art continues to desire new organic semiconductors, particularly those having good stability, processing properties, and/or charge transport characteristics in ambient conditions.

SUMMARY

In light of the foregoing, the present teachings provide thienocoronene-based semiconducting compounds and related heteroaromatic analogs that can exhibit properties such as good charge transport characteristics under ambient conditions, chemical stability, low-temperature processability, large solubility in common solvents, and processing versatility. As a result, field effect devices such as thin film transistors that incorporate the present compounds as the semiconductor layer can have high performance under ambient conditions, for example, demonstrating one or more of large electron mobilities, low threshold voltages, and high current on-off ratios.

In various embodiments, the present teachings provide compounds of formula I:

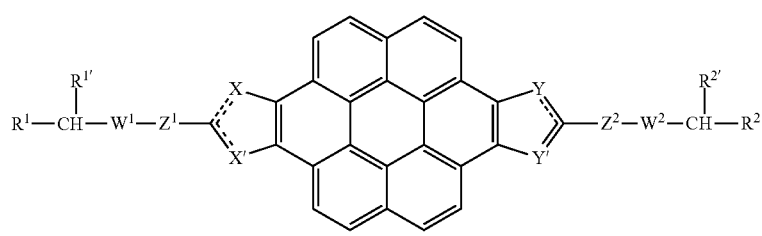

wherein $W^1$, $W^2$, X, X', Y, Y', $Z^1$, $Z^2$, $R^a$, $R^{a\prime}$, $R^b$, $R^{b\prime}$, $R^c$, $R^d$, $R^e$, $R^f$, $R^1$, $R^{1\prime}$, $R^2$, $R^{2\prime}$, and m are as defined herein.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF THE DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

DETAILED DESCRIPTION

Figure 1:
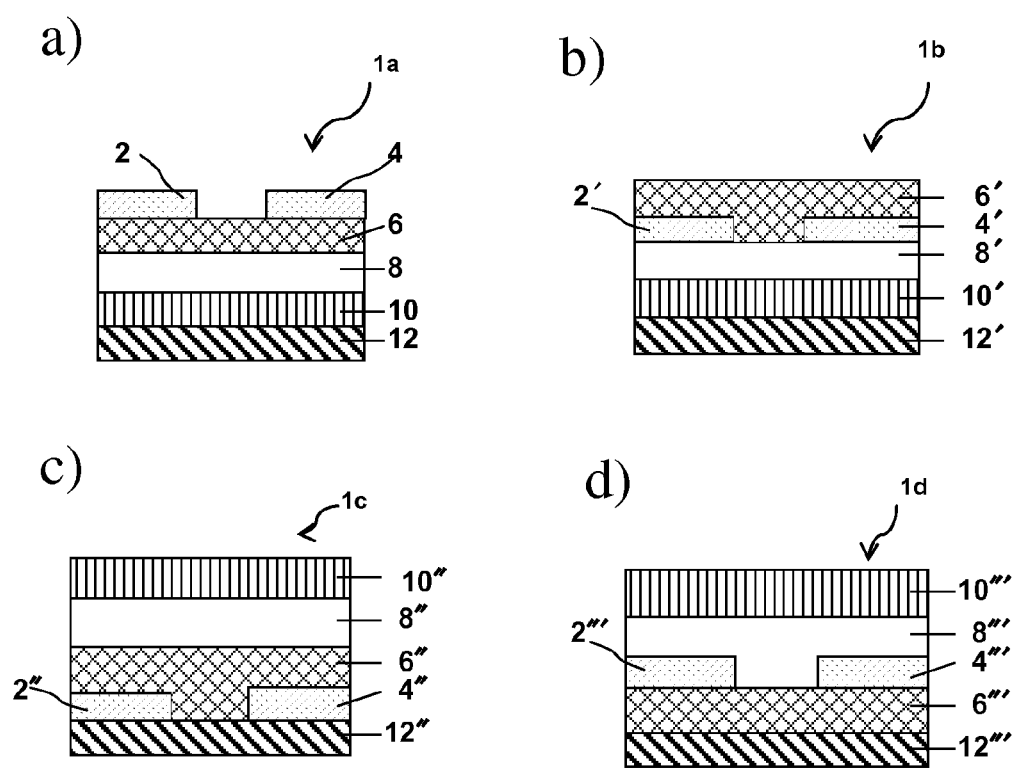
FIG. 1 illustrates four different configurations of thin film transistors: bottom-gate top contact (a), bottom-gate bottom-contact (b), top-gate bottom-contact (c), and top-gate top-contact (d); each of which can be used to incorporate polymers of the present teachings.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to –O— alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O— alkyl group can be substituted as described herein.

As used herein, "alkylthio" refers to an —S-alkyl group (which, in some cases, can be expressed as —S(O)$_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_8$-24 aryl group or an 8-24 membered heteroaryl group, each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is defined as a divalent alky group that can be optionally substituted as described herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

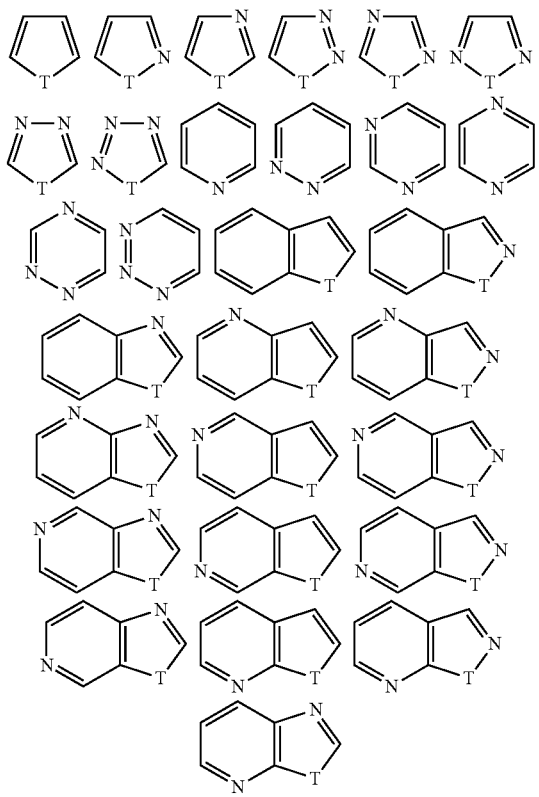

where T is O, S, NH, N-alkyl, N-aryl, N-(arylalkyl) (e.g., N-benzyl), $SiH_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^O)_2{}^+$, —$N(R^O)_3{}^+$, —$SO_3H$, —$SO_2R^O$, —$SO_3R^O$, —$SO_2NHR^O$, —$SO_2N(R^O)_2$, —COOH, —$COR^O$, —$COOR^O$, —$CONHR^O$, —$CON(R^O)_2$, $C_{1-40}$ haloalkyl groups, $C_{6-14}$ aryl groups, and 5-14 membered electron-poor heteroaryl groups; where $R^O$ is a $C_{1-40}$ alkyl group, a $C_{2-40}$ alkenyl group, a $C_{2-40}$ alkynyl group, a $C_{1-40}$ haloalkyl group, a $C_{1-40}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, —$OR^O$, —$NH_2$, —$NHR^O$, —$N(R^O)_2$, 5-14 membered electron-rich heteroaryl groups, $C_{1-40}$ alkyl groups, $C_{2-40}$ alkenyl groups, $C_{2-40}$ alkynyl groups, $C_{1-40}$ alkoxy groups, where $R^O$ is a $C_{1-40}$ alkyl group, a $C_{2-40}$ alkenyl group, a $C_{2-40}$ alkynyl group, a $C_{6-14}$ aryl group, or a $C_{3-14}$ cycloalkyl group.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one stereoisomer includes any other stereoisomer and any stereoisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

Throughout the specification, structures may or may not be presented with chemical names. Where any question arises as to nomenclature, the structure prevails.

The present teachings provide various semiconducting small molecule compounds as well as compositions and organic semiconductor materials prepared from such compounds and compositions. The organic semiconductor materials disclosed herein can exhibit useful electrical properties and can be solution-processable, e.g., spin-coatable and printable. In various embodiments, these materials can be considered p-type semiconductors. The semiconductor materials disclosed herein can be used to fabricate various organic electronic articles, structures and devices, including field-effect transistors, unipolar circuitries, complementary circuitries, and photovoltaic devices.

More specifically, the present teachings relate to compounds having formula I:

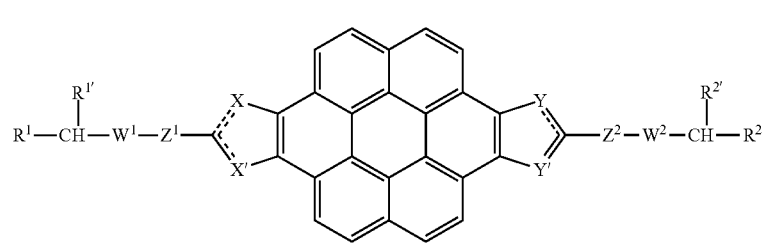

(I)

wherein:
W$^1$ and W$^2$ independently are selected from —(CR$^c$R$^d$)$_m$— and —(SiR$^e$R$^f$)—;
X and X' are selected from S, O, NR$^a$ and CR$^b$, provided that one of X and X' is selected from S, O, and NR$^a$, and the other X and X' is CR$^b$;
Y and Y' are selected from S, O, NR$^{a\prime}$ and CR$^{b\prime}$, provided that one of Y and Y' is selected from S, O, and NR$^{a\prime}$, and the other Y and Y' is CR$^{b\prime}$;
Z$^1$ and Z$^2$ independently are selected from O, S, —C≡C—, and a covalent bond;
R$^a$ and R$^{a\prime}$ independently are selected from H, a C$_{1-20}$ alkyl group, a C$_{2-20}$ alkenyl group, and a C$_{1-20}$ haloalkyl group;
R$^b$ and R$^{b\prime}$ independently are selected from H, a C$_{1-20}$ alkyl group, a C$_{2-20}$ alkenyl group, and a C$_{1-20}$ haloalkyl group;
R$^c$ and R$^d$ independently are selected from H, a C$_{1-20}$ alkyl group, and a C$_{1-20}$ haloalkyl group;
R$^e$ and R$^f$ independently are selected from H, a C$_{1-20}$ alkyl group, and a C$_{1-20}$ haloalkyl group;
R$^1$, R$^{1\prime}$, R$^2$, and R$^{2\prime}$ independently are selected from H, a linear C$_{1-40}$ alkyl group, a linear C$_{2-40}$ alkenyl group, and a linear C$_{1-40}$ haloalkyl group; and
m, at each occurrence, independently is selected from 0, 1, 2, 3, and 4.

In some embodiments, the present compounds can be represented by formula IIa or IIIa:

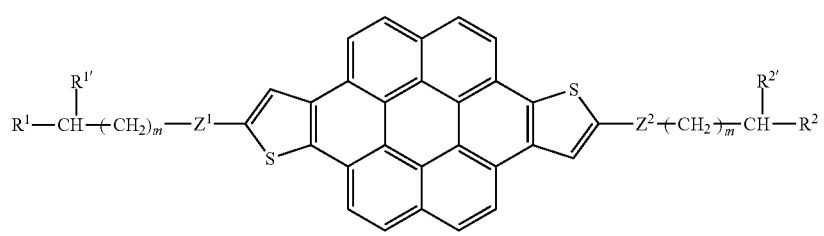

(IIa)

(IIIa)

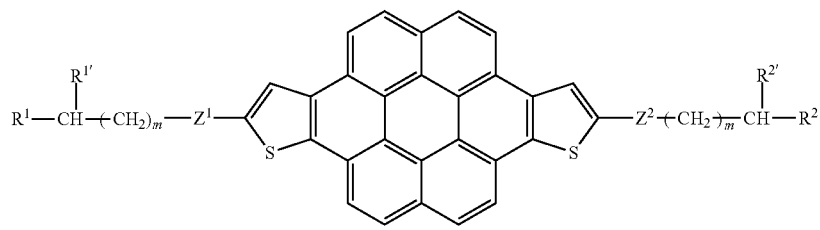

wherein $R^1$, $R^{1'}$, $R^2$, $R^{2'}$, $Z^1$, $Z^2$, and m are as defined herein. In certain embodiments, $R^1$, $R^{1'}$, $R^2$, and $R^{2'}$ independently can be selected from a linear $C_{1-40}$ alkyl group, a linear $C_{2-40}$ alkenyl group, and a linear $C_{1-40}$ haloalkyl group; $Z^1$ and $Z^2$ independently can be selected from O, S, and a covalent bond; and m, at each occurrence, independently can be selected from 0, 1, and 2. In certain embodiments, $R^1$ can be different from $R^{1'}$; and $R^2$ can be different from $R^{2'}$. For example, $R^{1'}$ and $R^{2'}$ can be selected from a linear $C_{1-6}$ alkyl group, a linear $C_{2-6}$ alkenyl group, and a linear $C_{1-6}$ haloalkyl group; whereas $R^1$ and $R^2$ can be selected from a linear $C_{3-40}$ alkyl group, a linear $C_{4-40}$ alkenyl group, and a linear $C_{3-40}$ haloalkyl group. In particular embodiments, $R^{1'}$ and $R^{2'}$ can be selected from $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$; whereas $R^1$ and $R^2$ can be selected from a linear $C_{3-20}$ alkyl group, a linear $C_{4-20}$ alkenyl group, and a linear $C_{3-20}$ haloalkyl group.

In certain embodiments, the present compounds can be represented by formula IIb or IIIb:

(IIb)

(IIIb)

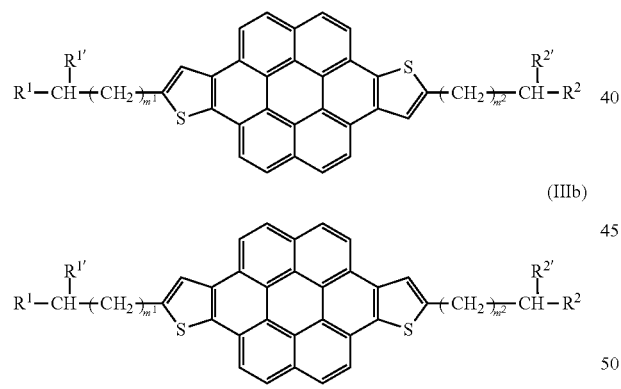

wherein $m^1$ and $m^2$ independently can be selected from 0, 1, and 2; and $R^1$, $R^{1'}$, $R^2$, and $R^{2'}$ are as defined herein. For example, $R^1$ and $R^2$ independently can be selected from a linear $C_{3-40}$ alkyl group, a linear $C_{4-40}$ alkenyl group, and a linear $C_{3-40}$ haloalkyl group; $R^{1'}$ and $R^{2'}$ independently can be selected from $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$. In particular embodiments, the present compounds can be optically pure stereoisomers. For example, certain compounds of formula IIb and IIIb can be stereospecific and can be represented by formula IIc or IIIc:

(IIc)

(IIIc)

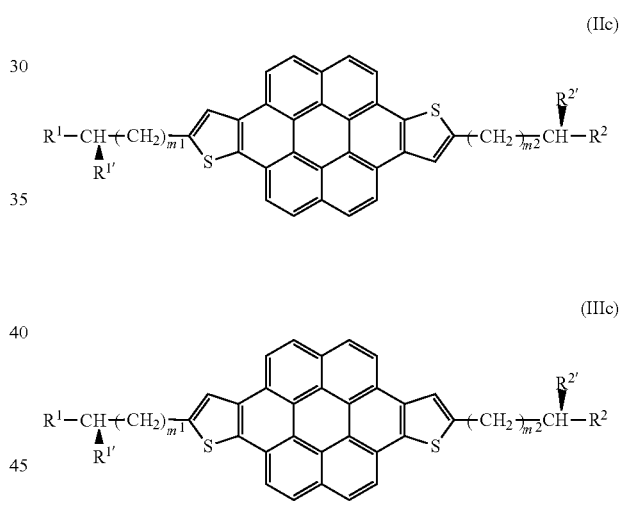

or their enantiomers, where $R^1$, $R^{1'}$, $R^2$, $R^{2'}$, $m^1$ and $m^2$ are as defined herein.

In some embodiments, the present compounds can be represented by formula IVa or Va:

(IVa)

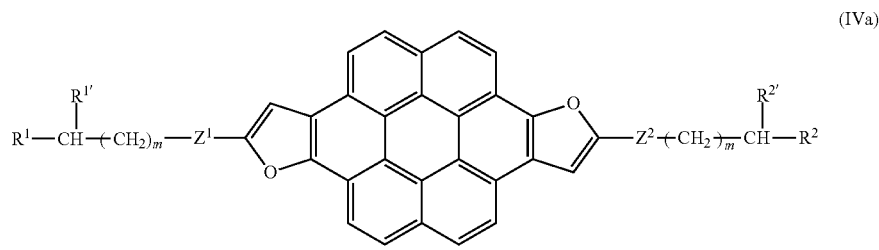

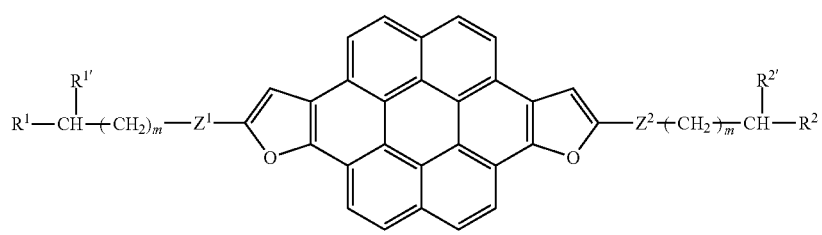

(Va)

wherein $R^1$, $R^{1'}$, $R^2$, $R^{2'}$, $Z^1$, $Z^2$, and m are as defined herein. In certain embodiments, $R^1$, $R^{1'}$, $R^2$, and $R^{2'}$ independently can be selected from a linear $C_{1-40}$ alkyl group, a linear $C_{2-40}$ alkenyl group, and a linear $C_{1-40}$ haloalkyl group; $Z^1$ and $Z^2$ independently can be selected from O, S, and a covalent bond; and m, at each occurrence, independently can be selected from 0, 1, and 2. In certain embodiments, R' can be different from $R^1$; and $R^2$ can be different from $R^{2'}$. For example, $R^{1'}$ and $R^{2'}$ can be selected from a linear $C_{1-6}$ alkyl group, a linear $C_{2-6}$ alkenyl group, and a linear $C_{1-6}$ haloalkyl group; whereas $R^1$ and $R^2$ can be selected from a linear $C_{3-40}$ alkyl group, a linear $C_{4-40}$ alkenyl group, and a linear $C_{3-40}$ haloalkyl group. In particular embodiments, $R^{1'}$ and $R^{2'}$ can be selected from $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$; whereas $R^1$ and $R^2$ can be selected from a linear $C_{3-20}$ alkyl group, a linear $C_{4-20}$ alkenyl group, and a linear $C_{3-20}$ haloalkyl group.

In certain embodiments, the present compounds can be represented by formula IVb or Vb:

(IVb)

(Vb)

wherein $m^1$ and $m^2$ independently can be selected from 0, 1, and 2; and $R^1$, $R^{1'}$, $R^2$, and $R^{2'}$ are as defined herein. For example, $R^1$ and $R^2$ independently can be selected from a linear $C_{3-40}$ alkyl group, a linear $C_{4-40}$ alkenyl group, and a linear $C_{3-40}$ haloalkyl group; $R^{1'}$ and $R^{2'}$ independently can be selected from $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$. In particular embodiments, the present compounds can be optically pure stereoisomers. For example, certain compounds of formula IVb and Vb can be stereospecific and can be represented by formula IVc or Vc:

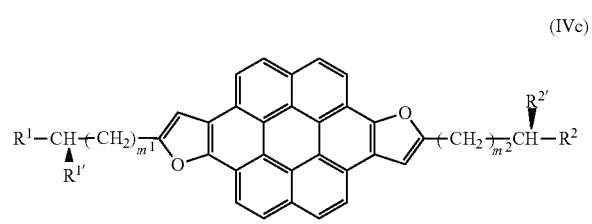

(IVc)

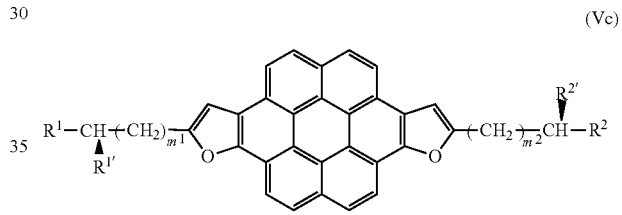

(Vc)

or their enantiomers, where $R^1$, $R^{1'}$, $R^2$, $R^{2'}$, $m^1$ and $m^2$ are as defined herein.

To illustrate, the groups $-(CH_2)_m CHR^1 R^{1'}$, $-(CH_2)_m CHR^2 R^{2'}$, $-(CH_2)_{m^1} CHR^1 R^{1'}$, and $-(CH_2)_{m^2} CHR^2 R^{2'}$ independently can be selected from a branched group such as an isopropyl group, an iso-butyl group, a sec-butyl group, a tert-butyl group, an iso-pentyl group, a sec-pentyl group, and a neo-pentyl group. In certain embodiments, the branched group can be a 1-alkyl substituted alkyl group (i.e., when m, $m^1$, or $m^2$ is 0), e.g.,

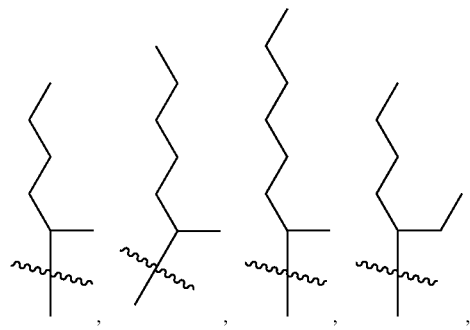

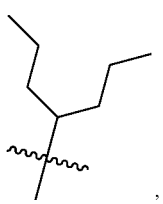, or 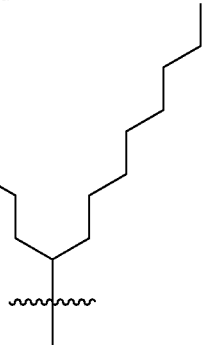;

a 2-alkyl substituted alkyl group (i.e., when m, m¹, or m² is 1), e.g.,

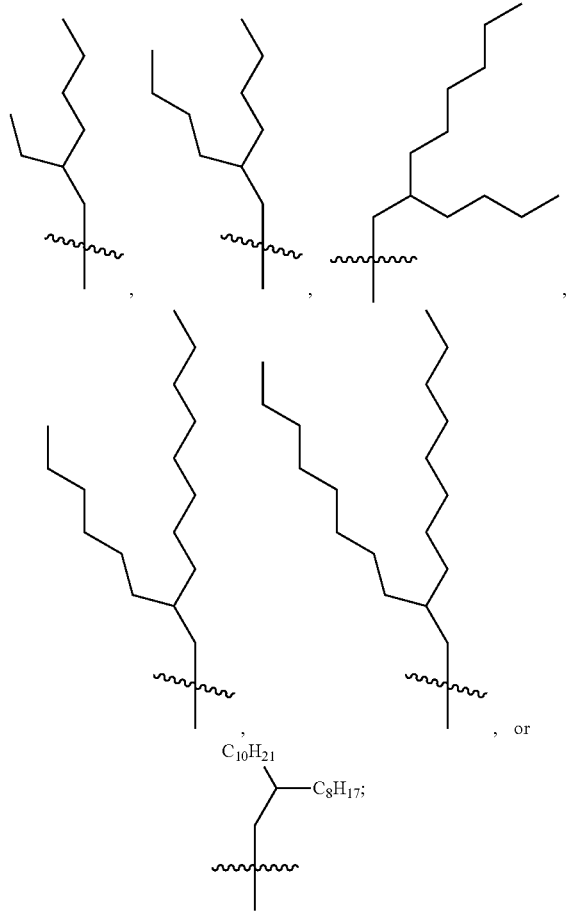

or a 3-alkyl substituted alkyl group (i.e., when m, m¹, or m² is 2), e.g.,

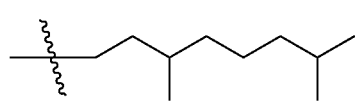

In various embodiments, the branched group can be stereospecific. An example could be

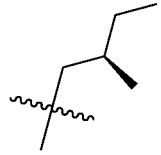

In addition, the groups $-(CH_2)_m CHR^1 R^{1'}$, $-(CH_2)_m CHR^2 R^{2'}$, $-(CH_2)_{m^1} CHR^1 R^{1'}$, and $-(CH_2)_{m^2} CHR^2 R^{2'}$ independently can be selected from corresponding branched $C_{3-20}$ haloalkyl groups, where one or more hydrogen atoms in the $C_{3-20}$ alkyl groups shown above are replaced by a halogen such as F.

In some embodiments, the present compounds can be represented by formula VI:

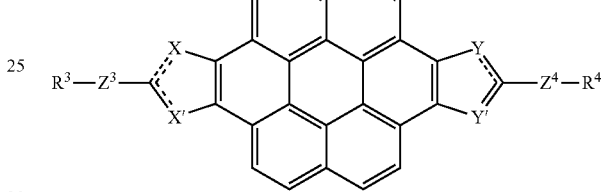

(VI)

wherein:

X and X' are selected from S, O, $NR^a$ and $CR^b$, provided that one of X and X' is selected from S, O, and $NR^a$, and the other X and X' is $CR^b$;

Y and Y' are selected from S, O, $NR^{a'}$ and $CR^{b'}$, provided that one of Y and Y' is selected from S, O, and $NR^{a'}$, and the other Y and Y' is $CR^{b'}$;

$Z^3$ and $Z^4$ independently are selected from O, S, and $-C \equiv C-$;

$R^a$ and $R^{a'}$ independently are selected from H, a $C_{1-20}$ alkyl group, a $C_{2-20}$ alkenyl group, and a $C_{1-20}$ haloalkyl group;

$R^b$ and $R^{b'}$ independently are selected from H, a $C_{1-20}$ alkyl group, a $C_{2-20}$ alkenyl group, and a $C_{1-20}$ haloalkyl group; and $R^3$ and $R^4$ independently are selected from a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group, and a $Si(C_{1-40} \text{ alkyl})_3$ group.

In certain embodiments, $Z^3$ and $Z^4$ can be O. For example, certain compounds of formula VI can be represented by formula VII or VIII:

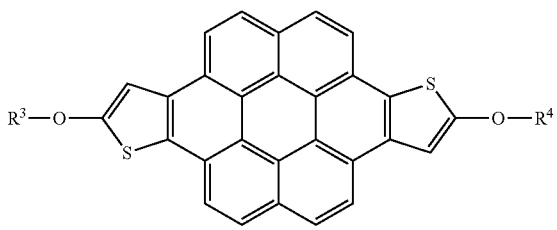

(VII)

-continued (VIII)

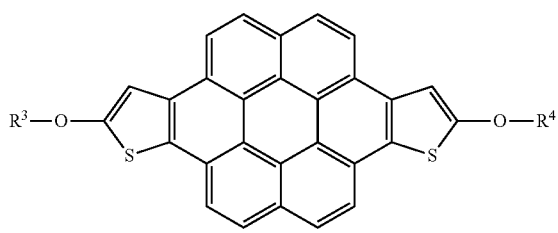

wherein $R^3$ and $R^4$ are as defined herein. For example, $R^3$ and $R^4$ independently can be selected from a linear or branched $C_{3-40}$ alkyl group, a linear or branched $C_{4-40}$ alkenyl group, and a linear or branched $C_{3-40}$ haloalkyl group. In particular embodiments, $R^3$ and $R^4$ independently can be selected from a linear or branched $C_{10-40}$ alkyl group, a linear or branched $C_{10-40}$ alkenyl group, and a linear or branched $C_{10-40}$ haloalkyl group.

In certain embodiments, $Z^3$ and $Z^4$ can be —C≡C—; and each of $R^3$ and $R^4$ can be $Si(C_{1-40}$ alkyl$)_3$, where each of the three $C_{1-40}$ alkyl groups can be linear or branched. In particular embodiments, each of $R^3$ and $R^4$ can be $Si(C_{3-20}$ alkyl$)_3$, where each of the three $C_{3-20}$ alkyl groups can be branched. For example, each of $R^3$ and $R^4$ can be $Si(i$-propyl$)_3$.

In certain embodiments, one of X and X' can be O, and the other of X and X' can be $CR^b$; while one of Y and Y' can be O, and the other of Y and Y' can be $CR^{b'}$, where $R^b$ and $R^{b'}$ independently can be selected from H and $CH_3$. In particular embodiments, compounds of formula VI can be represented by formula IX or X:

(IX)

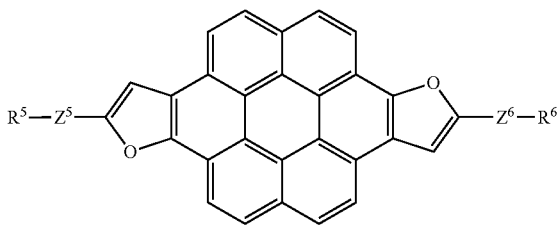

(X)

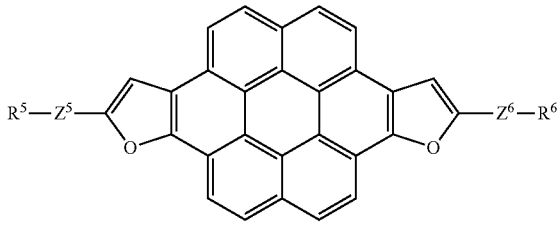

wherein:
$Z^5$ and $Z^6$ independently are selected from O, S, —C≡C—, and a covalent bond; and
$R^5$ and $R^6$ independently are selected from a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group; and a $Si(C_{1-40}$ alkyl$)_3$ group.

In particular embodiments, $R^5$ and $R^6$ independently can be selected from a linear or branched $C_{10-40}$ alkyl group, a linear or branched $C_{10-40}$ alkenyl group, and a linear or branched $C_{10-40}$ haloalkyl group.

In certain embodiments, one of X and X' can be $NR^a$, and the other of X and X' can be $CR^b$; while one of Y and Y' can be $NR^{a'}$, and the other of Y and Y' can be $CR^{b'}$, where $R^a$, $R^{a'}$, $R^b$, and $R^{b'}$ independently can be selected from H and $CH_3$. In particular embodiments, compounds of formula VI can be represented by formula XI or XII:

(XI)

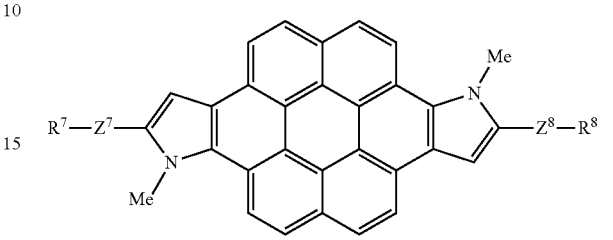

(XII)

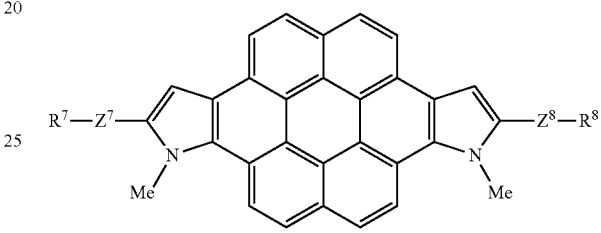

wherein:
$Z^7$ and $Z^8$ independently are selected from O, S, —C≡C—, and a covalent bond; and
$R^7$ and $R^8$ independently are selected from a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group; and a $Si(C_{1-40}$ alkyl$)_3$ group.

In particular embodiments, $R^5$ and $R^6$ independently can be selected from a linear or branched $C_{10-40}$ alkyl group, a linear or branched $C_{10-40}$ alkenyl group, and a linear or branched $C_{10-40}$ haloalkyl group.

Compounds of the present teachings can be prepared according to procedures described in Examples 1-7. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1H$ or $^{13}C$), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Various compounds according to the present teachings can have good charge transport properties and can be stable under ambient conditions ("ambient stable"), soluble in common solvents, and in turn solution-processable into various articles, structures, or devices. Accordingly, the present teachings provide for electronic devices, optical devices, and optoelectronic devices that include one or more compounds described herein as semiconductors. Examples of such electronic devices, optical devices, and optoelectronic devices include thin film semiconductors, thin film transistors (e.g., field effect transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators. In some embodiments, the present teachings provide for a thin film semiconductor including one or more compounds described herein and a field effect transistor device including the thin film semiconductor. In particular, the field effect transistor device has a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material includes an organic dielectric material, an inorganic dielectric material, or a hybrid organic/inorganic dielectric material. In other embodiments, the present teachings provide for photovoltaic devices and organic light emitting devices incorporating a thin film semiconductor that includes one or more compounds described herein.

Compounds of the present teachings generally have good solubility in a variety of common solvents. Thus, various embodiments of the present compounds can be processed via inexpensive solution-phase techniques into electronic devices, optical devices, or optoelectronic devices. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl)ether, diethyl ether, diisopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multi-layer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin coating, drop-casting, zone casting, dip coating, and blade coating.

The present compounds can exhibit versatility in their processing. Formulations including the present compounds can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more compounds disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., *PNAS,* 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT: PSS), polyaniline (PANI), polypyrrole (PPy)). One or more of the composites described herein can be embodied in various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

FIG. 1 illustrates the four common types of OFET structures: (top left) bottom-gate top-contact structure, (top right) bottom-gate bottom-contact structure, (bottom left) top-gate bottom-contact structure, and (bottom right) top-gate top-contact structure. As shown in FIG. 1, an OFET can include a gate dielectric component (e.g., shown as 8, 8', 8", and 8'''), a semiconductor component or semiconductor layer (e.g., shown as 6, 6', 6", and 6'''), a gate electrode or contact (e.g., shown as 10, 10', 10", and 10'''), a substrate (e.g., shown as 12, 12', 12", and 12'''), and source and drain electrodes or contacts (e.g., shown as 2, 2', 2", 2''', 4, 4', 4", and 4'''). As shown, in each of the configurations, the semiconductor component is in contact with the source and drain electrodes, and the gate dielectric component is in contact with the semiconductor component on one side and the gate electrode on an opposite side.

In certain embodiments, OTFT devices can be fabricated with one or more compounds disclosed herein on doped silicon substrates, using $SiO_2$ as the dielectric, in top-contact geometries. In particular embodiments, the active semiconductor layer which incorporates one or more compounds disclosed herein can be deposited at room temperature or at an elevated temperature. In other embodiments, the active semiconductor layer which incorporates one or more compounds disclosed herein can be applied by spin-coating or printing as described herein. For top-contact devices, metallic contacts can be patterned on top of the films using shadow masks.

In certain embodiments, OTFT devices can be fabricated with one or more compounds disclosed herein on plastic foils, using polymers as the dielectric, in top-gate bottom-contact geometries. In particular embodiments, the active semiconducting layer which incorporates one or more compounds disclosed herein can be deposited at room temperature or at an elevated temperature. In other embodiments, the active semiconducting layer which incorporates one or more compounds disclosed herein can be applied by spin-coating or printing as described herein. Gate and source/drain contacts can be made of Au, other metals, or conducting polymers and deposited by vapor-deposition and/or printing.

In various embodiments, a semiconducting component incorporating one or more compounds disclosed herein can exhibit p-type semiconducting activity, for example, a hole mobility of $10^{-4}$ $cm^2$/V-sec or greater and/or a current on/off ratio ($I_{on}/I_{off}$) of $10^3$ or greater.

Other articles of manufacture in which one or more compounds disclosed herein can be useful include photovoltaics (solar cells). The present compounds can exhibit broad optical absorption and/or a tuned redox properties and bulk carrier mobilities. Accordingly, the present compounds can be used, for example, as a p-type semiconductor in a photovoltaic design, which includes an adjcaent n-type semiconductor to form a p-n junction. The present compounds can be in the form of a thin film semiconductor, or a composite including the thin film semiconductor deposited on a substrate.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer ($^1H$, 500 MHz; $^{13}C$, 125 MHz). Electrospray mass spectrometry was performed on a Thermo Finnegan model LCQ Advantage mass spectrometer.

EXAMPLE 1

Synthesis of 1PB-Thienocoronene

Preparation of 4-thiophen-2-yl-heptan-4-ol

A solution of 2-bromothiophene (10.0 g, 61.5 mmol) in dry THF (60 mL) was cooled to $-78°$ C. under nitrogen. A solution of n-BuLi (2.5 M, 27.0 mL, 67.5 mmol) was then added slowly, and the resulting mixture was stirred at $-78°$ C. for 2 hours, before a solution of 4-heptanone (8.5 g, 74.4 mmol) in dry THF (10 mL) was added slowly. This mixture was stirred at $-78°$ C. for an additional 1 hour, and then allowed to warm to room temperature, and stirred at room temperature overnight. Most of the solvent was removed in vacuo, and the residue was subjected to flash column chromatography on silica gel with a hexane:EtOAc (3:1, v/v) mixture, leading to a colorless oil as the product (10.2 g, 83.5%).

$^1H$ NMR (CDCl$_3$, 500 MHz): 7.19 (dd, J=5.0 Hz, J=1.5 Hz, 1H). 6.96 (dd, J=5.0 Hz, J=3.5 Hz, 1H), 6.91 (dd, J=3.5 Hz, J=1.0 Hz, 1H), 1.73-1.86 (m, br, 4H), 1.20-1.40 (m, br, 4H), 0.90 (t, J=7.0 Hz, 6H).

Preparation of 2-(1-propylbutyl)thiophene

Under nitrogen, a suspension of LiAlH$_4$ (3.6 g, 94.9 mmol) in dry Et$_2$O (500 mL) was cooled to $0°$ C. by an ice/water bath.

AlCl$_3$ (24.9 g, 186.7 mmol) was then added in small portions. After addition, the mixture was stirred at 0° C. for 1 hour. A solution of 4-thiophen-2-yl-heptan-4-ol (10.2 g, 51.3 mmol) was then added dropwise. The mixture was stirred at 0° C. for 2 hours, and allowed to warm to room temperature and stirred at room temperature overnight. After cooling to 0° C., the reaction was quenched by adding water. The reaction mixture was washed with water and brine, dried over Na$_2$SO$_4$, and concentrated on a rotary evaporator. The residue was subjected to column chromatography on silica gel with hexane as the eluent, leading to a colorless oil as the product (9.1 g, 97.2%).

$^1$H NMR (CDCl$_3$, 500 MHz): 7.13 (d, J=5.0 Hz, 1H). 6.92 (dd, J=5.0 Hz, J=3.5 Hz, 1H), 6.76 (dd, J=3.5 Hz, 1H), 2.87 (m, br, 1H), 1.50-1.67 (m, br, 4H), 1.21-1.30 (m, br, 4H), 0.88 (t, J=7.0 Hz, 6H).

Preparation of 2-(1-propylbutyl)-5-trimethystannylthiophene

A solution of 2-(1-propylbutyl)thiophene (3.4 g, 18.7 mmol) in dry THF (60 mL) was cooled to −78° C., and a solution of n-BuLi (2.5 M, 11.1 mL, 27.8 mmol) was then added slowly. This mixture was stirred at −78° C. for additional 10 minutes, and then allowed to warm to room temperature and stirred at room temperature for 30 minutes, before it was cooled back to −78° C. A solution of trimethylstannyl chloride (1.0 M, 28 mL, 28.0 mmol) was added slowly. This mixture was stirred at −78° C. for 1 hour, and then allowed to warm to room temperature, and stirred at room temperature overnight. The reaction was quenched by water. The resulting mixture was diluted with hexane, washed with water, dried over Na$_2$SO$_4$, and concentrated on a rotary evaporator, leading to a slightly yellow oil (6.27 g, 97.5%), which was directly used in the next step without further purification.

$^1$H NMR (CDCl$_3$, 500 MHz): 7.01 (d, J=3.5 Hz, 1H), 6.88 (d, J=3.5 Hz, 1H), 2.92 (m, br, 2H), 1.48-1.65 (m, br, 4H), 1.20-1.33 (m, br, 4H), 0.87-0.92 (t, J=7.0 Hz, 6H), 0.35 (s, 9H).

Preparation of 1,7(or 1,6)-bis[5-(1-propylbutyl)thiophen-2-yl]perylene-3,4:9,10-tetracarboxylic dianhydride A mixture of PDA-Br$_2$ (2.47 g, 4.49 mmol), 2-(1-propylbutyl)-5-trimethystannylthiophene (6.2 g, 17.96 mmol), Pd(PPh$_3$)$_4$ (0.50 g, 0.43 mmol) in dry toluene (150 mL) was heated to reflux for 52 hours under argon. After cooling to room temperature, a HCl solution (2M, 20 mL) was added, and the resulting mixture was stirred at room temperature for 30 minutes. The reaction mixture was diluted with chloroform, and this mixture was washed with water, dried over Na$_2$SO$_4$, and passed through a short pad of silica gel. The filtrate was concentrated in vacuo, leading to a dark solid as the product, which was used directly in the next step without further purification (2.15, 63.6%)

$^1$H NMR (CDCl$_3$, 500 MHz): 8.72 (s, 2H), 8.22 (s, br, 4H), 7.17 (d, J=3.5 Hz, 2H), 6.88 (d, J=3.5 Hz, 2H), 2.91 (m, br, 2H), 1.63-1.72 (m, br, 4H), 1.46-1.57 (m, br, 4H), 1.28-1.42 (m, br, 8H), 0.94 (t, J=7.0 Hz, 12H).

Preparation of 1,7(or 1,6)-bis[5-(1-propylbutyl)thiophen-2-yl]perylene

A mixture of 1,7(or 1,6)-bis[5-(1-propylbutyl)thiophen-2-yl]perylene-3,4:9,10-tetracarboxylic dianhydride (1.64 g, 2.18 mmol), Cu$_2$O (1.50 g, 10.48 mmol), bipyridyl (0.80 g, 5.12 mmol), water (4.5 mL), and quinoline (38 mL) was heated to reflux under nitrogen for 48 hours. After cooling to room temperature, the reaction mixture was diluted with chloroform, and the resulting mixture was washed with dilute HCl and water, dried over Na$_2$SO$_4$, and concentrated in vacuo. The residue was subjected to column chromatography on silica gel with a chloroform:hexane (1:4, v/v) mixture, leading to a sticky orange solid (0.98 g, 73.4%).

$^1$H NMR (CDCl$_3$, 500 MHz): 7.70 (dd, J=7.5 Hz, J=0.5, 2H), 7.66 (d, J=8.5 Hz, 2H), 7.57 (d, J=7.5 Hz, 2H), 7.52 (d, J=8.0 Hz, 2H), 7.10 (t, J=8.0 Hz, 2H), 6.97 (d, J=3.5 Hz, 2H), 6.75 (d, J=3.5 Hz, 2H), 2.86 (m, br, 2H), 1.58-1.67 (m, br, 4H), 1.46-1.57 (m, br, 4H), 1.25-1.45 (m, br, 8H), 0.92 (t, J=7.5 Hz, 12H).

Preparation of 1PB-thienocoronene

A solution of 1,7(or 1,6)-bis[5-(1-propylbutyl)thiophen-2-yl]perylene (0.98 g, 1.60 mmol), iodine (0.91 g, 3.59 mmol), and benzene (700 mL) was sonicated for 5 minutes, and placed in a UV-reactor for 15 hours. The reaction mixture was washed with saturated Na$_2$SO$_3$ aqueous solution and water, dried over anhydrous Na$_2$SO$_4$, and concentrated in vacuo. The residue was subjected to flash column chromatography on silica gel with a chloroform:hexane (1:4, v/v) mixture as eluent, leading to a slightly yellow solid as the product (0.74 g, 76.3%).

$^1$H NMR (CDCl$_3$, 500 MHz): 8.92 (d, J=8.5 Hz, 2H), 8.71 (d, J=8.5 Hz, 2H), 8.57 (d, J=8.5 Hz, 2H), 8.56 (d, J=8.5 Hz, 2H), 8.18 (s, 2H), 3.36 (m, br, 2H), 1.94-2.00 (m, br, 8H), 1.51-1.60 (m, br, 8H), 1.04-1.07 (t, J=7.5 Hz, 12H). Elemental Analysis (calc. C, 82.85; H, 6.62; N, 0.00). found C, 83.07; H, 6.64; N, 0.00.

EXAMPLE 2

Synthesis of 2BO-Thienocoronene

Preparation of 2-(2-butyloctyl)thiophene

A solution of thiophene (5.71 g, 67.9 mmol) in dry THF (60 mL) was cooled to −78° C. under nitrogen. A solution of n-BuLi (26.0 mL, 2.5 M, 65.0 mmol) was then added dropwise. After addition, the reaction mixture was stirred at −78° C. for additional 1 hour, before a solution of 2-butyloctyliodide (16.0 g, 54.0 mmol) in dry THF (30 mL) was added slowly. This mixture was stirred at −78° C. for 1 hour, and then allowed to warm to room temperature slowly and stirred at room temperature for 38 hours. The reaction mixture was poured into water, and the resulting mixture was extracted with ether. The organic layer was washed with water and brine, dried over MgSO$_4$, and concentrated on a rotary evaporator. The residue was subjected to column chromatography on silica gel with hexane as the eluent, leading to a colorless oil as the product (4.95 g, 36.3%).

$^1$H NMR (CDCl$_3$, 500 MHz): 7.12 (dd, J=5.5 Hz, J=1.5 Hz, 1H), 6.92 (dd, J=5.0 Hz, J=3.5 Hz, 1H), 6.76 (dd, J=3.5 Hz, J=0.5 Hz, 1H), 2.76 (d, J=6.5 Hz, 2H), 1.63 (m, 1H), 1.24-1.32 (m, br, 16H), 0.87-0.91 (m, br, 6H).

Preparation of 2-(2-butyloctyl)-5-trimethylstannylthiophen

A solution of 2-(2-butyloctyl)thiophene (1.52 g, 6.02 mmol) in dry THF (30 mL) was cooled to −78° C., and a solution of n-BuLi (2.5 M, 3.6 mL, 9.0 mmol) was then added slowly. This mixture was stirred at −78° C. for additional 10 minutes, and allowed to warm to room temperature and stirred at room temperature for 30 minutes, before it was cooled back to −78° C. again. A solution of trimethylstannyl chloride (1.0 M, 9 mL, 9.0 mmol) was added slowly. This mixture was stirred at −78° C. for 1 hour, and then allowed to warm to room temperature, and stirred at room temperature overnight. The reaction was quenched by water. The resulting reaction mixture was diluted with hexane, washed with water, dried over $Na_2SO_4$, and concentrated on a rotary evaporator, leading to a slightly yellow oil (2.48 g, 99.2%), which was directly used in the next step without further purification.

$^1$H NMR ($CDCl_3$, 500 MHz): 7.02 (d, J=3.5 Hz, 1H), 6.88 (d, J=3.0 Hz, 1H), 2.80 (d, J=6.5 Hz, 2H), 1.64 (m, br, 1H), 1.23-1.34 (m, br, 16H), 0.87-0.92 (m, br, 6H), 0.35 (s, 9H).

Preparation of 1,7(or 1,6)-bis[5-(2-butyloctyl)thiophen-2-yl]perylene-3,4:9,10-tetracarboxylic dianhydride A mixture of PDA-$Br_2$ (0.82 g, 1.49 mmol), 2-(2-butyloctyl)-5-trimethylstannylthiophene (2.48 g, 5.97 mmol), Pd(PPh$_3$)$_4$ (0.17 g, 0.15 mmol) in dry toluene (50 mL) was heated at reflux temperature for 40 hours under argon. After cooling to room temperature, a HCl solution (2M, 20 mL) was added, and the resulting mixture was stirred at room temperature for 30 minutes. The reaction mixture was diluted with chloroform, and this mixture was washed with water, dried over $Na_2SO_4$, passed through a short pad of silica gel. The filtrate was concentrated in vacuo, leading to a dark solid as the product, which was used directly in the next step without further purification (1.15, 86.5%).

$^1$H NMR ($CDCl_3$, 500 MHz): 8.71 (s, 2H), 8.28 (d, J=1.5 Hz, 4H), 7.18 (d, J=3.0 Hz, 2H), 6.86 (d, J=3.5 Hz, 2H), 2.82 (d, J=6.5 Hz, 4H), 1.64 (m, br, 2H), 1.24-1.40 (m, br, 16H), 0.86-0.95 (m, br, 12H).

Preparation of 1,7(or 1,6)-bis[5-(2-butyloctyl)thiophen-2-yl]perylene

A mixture of 1,7(or 1,6)-bis[5-(2-butyloctyl)thiophen-2-yl]perylene-3,4:9,10-tetracarboxylic dianhydride (0.42 g, 0.47 mmol), $Cu_2O$ (0.31 g, 2.17 mmol), bipyridyl (0.17 g, 1.09 mmol), water (0.8 mL), and quinoline (8 mL) was heated to reflux under nitrogen for 49 hours. After cooling to room temperature, the reaction mixture was diluted with chloroform, and the resulting mixture was washed with dilute HCl and water, dried over $Na_2SO_4$, and concentrated in vacuo. The residue was subjected to column chromatography on silica gel with a chloroform:hexane (1:2, v/v, flash) mixture, leading to an orange sticky solid (0.29 g, 81.9%).

$^1$H NMR ($CDCl_3$, 500 MHz): 7.74 (d, J=7.0 Hz, 2H), 7.66 (d, J=8.5 Hz, 2H), 7.58 (d, J=8.0 Hz, 2H), 7.52 (d, J=7.5 Hz, 2H), 7.14 (t, J=7.5 Hz, 2H), 6.98 (d, J=3.5 Hz, 2H), 6.73 (d, J=3.0 Hz, 2H), 2.77 (d, J=6.5 Hz, 4H), 1.63 (m, br, 2H), 1.25-1.39 (m, br, 16H), 0.86-0.96 (m, br, 12H).

Preparation of 2BO-thienocoronene

A solution of 1,7(or 1,6)-bis[5-(2-butyloctyl)thiophen-2-yl]perylene (0.68 g, 0.90 mmol), iodine (0.51 g, 2.0 mmol), and benzene (400 mL) was sonicated for 5 minutes, and placed in a UV-reactor for 15 hours. The reaction mixture was washed with saturated $Na_2SO_3$ aqueous solution and water, dried over anhydrous $Na_2SO_4$, and concentrated in vacuo. The residue was subjected to flash column chromatography on silica gel with a chloroform:hexane (1:4, v/v) mixture as the eluent, leading to a slightly yellow solid as the product (0.49 g, 72.5%).

$^1$H NMR ($CDCl_3$, 500 MHz): 8.97 (d, J=8.5 Hz, 2H), 8.78 (d, J=8.5 Hz, 2H), 8.67 (d, J=8.5 Hz, 2H), 8.65 (d, J=8.5 Hz, 2H), 8.16 (s, 2H), 3.23 (d, J=6.5 Hz, 4H), 2.03 (m, br, 2H), 1.30-1.62 (m, br, 16H), 0.97 (t, J=7.0 Hz, 12H). Elemental Analysis (calc. C, 83.37; H, 8.07; N, 0.00). found C, 83.15; H, 8.29; N, 0.00.

EXAMPLE 3

Synthesis of 1MP-Thienocoronene

Preparation of 2-thiophen-2-yl-hexan-2-ol

A solution of 2-bromothiophene (24.3 g, 0.15 mol) in dry THF (120 mL) was cooled to −78° C. under nitrogen. A solution of n-BuLi (2.5 M, 66.0 mL, 0.17 mol) was then added slowly, and the resulting mixture was stirred at −78° C. for 2 hours, before 2-hexanone (18.1 g, 0.18 mol) was added slowly. This mixture was stirred at −78° C. for an additional 1 hour, and then allowed to warm to room temperature, and stirred at room temperature overnight. Most of the solvent was removed in vacuo, and the residue was subjected to flash column chromatography on silica gel with a hexane:EtOAc (4:1, slowly up to 3:1, v/v) mixture, leading to a slightly yellow oil as the product (21.4 g, 77.7%).

$^1$H NMR ($CDCl_3$, 500 MHz): 7.20 (d, J=5.0 Hz, 1H). 6.96 (t, J=4.5 Hz, 1H), 6.91 (d, J=3.5 Hz, 1H), 1.86 (t, J=8.5 Hz, 2H), 1.64 (s, 3H), 1.25-1.38 (m, br, 4H), 0.89 (t, J=7.0 Hz, 3H).

Preparation of 2-(1-methypentyl)thiophene

Under nitrogen, a suspension of LiAlH$_4$ (4.9 g, 0.13 mol) in dry Et$_2$O (700 mL) was cooled to 0° C. by an ice/water bath. AlCl$_3$ (34.4 g, 0.26 mol) was then added in small portions. After addition, the mixture was stirred at 0° C. for 1 hour. A solution of 2-thiophen-2-yl-hexan-2-ol in dry Et$_2$O (13.1 g, 70.81 mmol) was then added dropwise. The mixture was stirred at 0° C. for 2 hours, and allowed to warm to room temperature, and stirred at room temperature overnight. After cooling to 0° C., the reaction was quenched by adding water. The reaction mixture was washed with water and brine, dried over $Na_2SO_4$, and concentrated on a rotary evaporator. The residue was subjected to column chromatography on silica gel with hexane as the eluent, leading to a colorless oil as the product (6.0 g, 50.3%).

$^1$H NMR ($CDCl_3$, 500 MHz): 7.13 (dd, J=5.0 Hz, J=0.5 Hz, 1H), 6.93 (dd, J=5.0 Hz, J=3.5 Hz, 1H), 6.80 (d, J=3.5 Hz, 1H), 3.02 (m, 1H), 1.54-1.70 (m, br, 2H), 1.32 (d, J=6.5 Hz, 3H), 1.22-1.34 (m, br, 4H), 0.86-0.90 (t, J=7.5 Hz, 3H).

Preparation of 2-(1-methylpentyl)-5-trimethylstannyl

A solution of 2-(1-methypentyl)-thiophene (2.8 g, 16.6 mmol) in dry THF (60 mL) was cooled to −78° C., and a solution of n-BuLi (2.5 M, 10 mL, 25.0 mmol) was then added slowly. This mixture was stirred at −78° C. for additional 10 minutes, and then allowed to warm to room temperature and stirred at room temperature for 40 minutes, before it was cooled back to −78° C. A solution of trimethylstannyl chloride (1.0 M, 25 mL, 25.0 mmol) was added slowly. This mixture was stirred at −78° C. for 1 hour, and then allowed to warm to room temperature, and stirred at room temperature overnight. The reaction was quenched by water, and the reaction mixture was diluted with hexane, washed with water, dried over $Na_2SO_4$, and concentrated on a rotary evaporator, leading to a slightly yellow oil as the product (5.4 g, 98.0%), which was used directly in the next step without further purification.

$^1$H NMR ($CDCl_3$, 500 MHz): 7.03 (d, J=3.5 Hz, 1H), 6.92 (d, J=3.0 Hz, 1H), 3.06 (m, 1H), 1.55-1.70 (m, br, 2H), 1.22-1.37 (m, br, 7H), 0.87-0.91 (t, J=6.5 Hz, 3H), 0.35 (s, 9H).

Preparation of 1,7(or 1,6)-bis[5-(1-methylpentyl) thiophen-2-yl]perylene-3,4:9,10-tetracarboxylic dianhydride A mixture of $PDA-Br_2$ (0.98 g, 1.8 mmol), 2-(1-methylpentyl)-5-trimethylstannyl (2.4 g, 7.2 mmol), $Pd(PPh_3)_4$ (0.22 g, 0.19 mmol) in dry toluene (60 mL) was heated at reflux temperature for 24 hours under argon. After cooling to room temperature, a HCl solution (2M, 20 mL) was added, and the resulting mixture was stirred at room temperature for 20 minutes. The reaction mixture was diluted with chloroform, and this mixture was washed with water, dried over $Na_2SO_4$, passed through a short pad of silica gel. The filtrate was concentrated in vacuo, leading to a dark solid as the product, which was used directly in the next step without further purification (1.1 g, 84.5%).

$^1$H NMR ($CDCl_3$, 500 MHz): 8.71 (s, 2H), 8.26 (s, br, 4H), 7.17 (d, J=3.5 Hz, 2H), 6.89 (d, J=3.5 Hz, 2H), 3.06 (m, 2H), 1.63 (m, br, 4H), 1.30-1.40 (m, br, 14H), 0.93-0.96 (t, J=7.0 Hz, 6H).

Preparation of 1,7(or 1,6)-bis[5-(1-methylpentyl)thiophen-2-yl]perylene

A mixture of 1,7(or 1,6)-bis[5-(1-methylpentyl)thiophen-2-yl]perylene-3,4:9,10-tetracarboxylic dianhydride (0.76 g, 1.04 mmol), $Cu_2O$ (0.70 g, 4.89 mmol), bipyridyl (0.38 g, 2.43 mmol), water (2 mL), quinoline (18 mL) was stirred at reflux temperature under nitrogen for 48 hours. After cooling to room temperature, the reaction mixture was diluted with chloroform, and the resulting mixture was washed with diluted HCl, water, and brine in sequence, and dried over $Na_2SO_4$. Solvents were removed in vacuo, and the residue was subjected to column chromatography on silica gel with a chloroform:hexane (1:2, v/v) mixture, leading to an orange solid (0.47 g, 77.1%).

$^1$H NMR ($CDCl_3$, 500 MHz): 7.71 (d, J=7.5 Hz, 2H), 7.66 (d, J=8.5 Hz, 2H), 7.58 (d, J=8.0 Hz, 2H), 7.52 (d, J=8.0 Hz, 2H), 7.14 (t, J=7.5 Hz, 2H), 6.98 (d, J=3.5 Hz, 2H), 6.76 (d, J=3.0 Hz, 2H), 3.01 (m, 2H), 1.62 (m, br, 4H), 1.30-1.38 (m, br, 14H), 0.90-0.96 (t, J=7.0 Hz, 6H).

Preparation of 1MP-thienocoronene

A solution of 1,7(or 1,6)-bis[5-(1-methylpentyl)thiophen-2-yl]perylene (0.47 g, 0.80 mmol), iodine (0.46 g, 1.8 mmol), and benzene (420 mL) was sonicated for 5 minutes, and placed in a UV-reactor for 18 hours. Most of the solvents were removed in vacuo, and the residue was subjected to flash column chromatography on silica gel with a chloroform:hexane=2:7 (v/v) mixture as eluent, leading to a slightly yellow solid as the product (0.20 g, 43.3%).

$^1$H NMR ($CDCl_3$, 500 MHz): 8.96 (d, J=8.5 Hz, 2H), 8.77 (d, J=8.5 Hz, 2H), 8.65 (d, J=8.0 Hz, 2H), 8.63 (d, J=8.5 Hz, 2H), 8.21 (s, 2H), 3.49 (m, 2H), 2.03 (m, 2H), 1.96 (m, 2H), 1.70 (d, J=7.0 Hz, 6H), 1.48-1.60 (m, br, 8H), 0.95-1.00 (t, J=7.0 Hz, 6H). Elemental Analysis (calc. C, 82.71; H, 6.25; N, 0.00). found C, 82.88; H, 6.31; N, 0.00.

EXAMPLE 4

Synthesis of (S)-2MB-Thienocoronene

Preparation of (S)-2-(2-methylbutyl)thiophene

A solution of thiophene (10.6 g, 0.13 mol) in dry THF (100 mL) was cooled to −78° C. under nitrogen. A solution of n-BuLi (28.0 mL, 2.5 M, 70.0 mmol) was then added dropwise. After addition, the reaction mixture was stirred at −78° C. for additional 1 hour, before a solution of (S)-2-methylbutyliodide (10.0 g, 50.5 mmol) in dry THF (20 mL) was added slowly. This mixture was stirred at −78° C. for 1 hour, and then allowed to warm to room temperature slowly and stirred at room temperature overnight. The reaction was quenched by water and the mixture was poured into water (100 mL), and the resulting mixture was extracted with ether (300 mL). The organic layer was washed with water and brine, dried over $MgSO_4$, and concentrated on a rotary evaporator. The residue was subjected to column chromatography on silica gel with hexane as the eluent, leading to a colorless oil as the product (4.27 g, 54.8%).

$^1$H NMR ($CDCl_3$, 500 MHz): 7.12 (dd, J=5.5 Hz, J=1.0 Hz, 1H), 6.92 (dd, J=5.0 Hz, J=3.5 Hz, 1H), 6.76 (dd, J=3.5 Hz, J=0.5 Hz, 1H), 2.80-2.85 (dd, J=14.5 Hz, J=6.5 Hz, 1H), 2.61-2.66 (dd, J=14.5 Hz, J=7.5 Hz, 1H), 1.60-1.73 (m, 1H), 1.36-1.49 (m, 1H), 1.14-1.24 (m, 1H), 0.89-0.94 (m, br, 6H).

Preparation of (S)-2-(2-methylbutyl)-5-trimethylstannylthiophene

A solution of (S)-2-(2-methylbutyl)thiophene (4.27 g, 27.7 mmol) in dry THF (100 mL) was cooled to −78° C., and a solution of n-BuLi (2.5 M, 16.6 mL, 41.5 mmol) was then added slowly. This mixture was stirred at −78° C. for additional 10 minutes, and then allowed to warm to room temperature and stirred at room temperature for 30 minutes, before it was cooled back to −78° C. A solution of trimethylstannyl chloride (1.0 M, 43 mL, 43.0 mmol) was added slowly. This mixture was stirred at −78° C. for 2 hours, and then allowed to warm to room temperature, and stirred at room temperature overnight. The reaction was quenched by water (20 mL), and the reaction mixture was diluted with hexane, washed with water, dried over $Na_2SO_4$, and concentrated on a rotary evaporator, leading to a slightly yellow oil (8.7 g, 99.1%), which was used directly in the next step without further purification.

$^1$H NMR ($CDCl_3$, 500 MHz): 7.02 (d, J=3.5 Hz, 1H), 6.89 (d, J=3.0 Hz, 1H), 2.84-2.88 (dd, J=14.5 Hz, J=6.0 Hz, 1H), 2.65-2.70 (dd, J=14.5 Hz, J=7.5 Hz, 1H), 1.65-1.74 (m, 1H), 1.40-1.52 (m, 1H), 1.25-1.35 (m, 1H), 0.89-0.94 (m, br, 6H). 0.35 (s, 9H).

Preparation of 1,7(or 1,6)-bis[5-((s)-2-methylbutyl) thiophen-2-yl]perylene-3,4:9,10-tetracarboxylic dianhydride A mixture of $PDA-Br_2$ (3.7 g, 6.7 mmol), (S)-2-(2-methylbutyl)-5-trimethylstannylthiophene (8.7 g, 27.4 mmol), $Pd(PPh_3)_4$ (0.70 g, 0.61 mmol) in dry toluene (150 mL) was heated at reflux temperature under argon for 40 hours. After cooling to room temperature, a HCl solution (2M, 20 mL) was added, and the resulting mixture was stirred at room temperature for 30 minutes. The reaction mixture was diluted with chloroform, then washed with water, dried over $Na_2SO_4$, and passed through a short pad of silica gel. The filtrate was concentrated in vacuo, leading to a dark solid as the product, which was used directly in the next step without further purification (3.87 g, 82.6%).

$^1$H NMR (CDCl$_3$, 500 MHz): 8.71 (s, 2H), 8.27 (s, 4H), 7.18 (d, J=3.5 Hz, 2H), 6.86 (d, J=3.5 Hz, 2H), 2.85-2.91 (dd, J=14.5 Hz, J=6.5 Hz, 2H), 2.67-2.73 (dd, J=14.5 Hz, J=7.5 Hz, 2H), 1.64-1.73 (m, br, 2H), 1.44-1.53 (m, br, 2H), 1.21-1.30 (m, br, 2H), 0.94-0.99 (m, br, 12H).

Preparation of 1,7(or 1,6)-bis[5-((s)-2-methylbutyl)thiophen-2-yl]perylene

A mixture of 1,7(or 1,6)-bis[5-((S)-2-methylbutyl)thiophen-2-yl]perylene-3,4:9,10-tetracarboxylic dianhydride (0.71 g, 1.02 mmol), Cu$_2$O (0.70 g, 4.89 mmol), bipyridyl (0.38 g, 2.43 mmol), water (2.0 mL), and quinoline (18 mL) was heated at reflux temperature under nitrogen for 30 hours. After cooling to room temperature, the reaction mixture was diluted with chloroform, washed with diluted HCl and water, dried over Na$_2$SO$_4$, and concentrated in vacuo. The residue was subjected to column chromatography on silica gel with a chloroform:hexane=3:8 (v/v) mixture, leading to an orange solid (0.16 g, 28.2%).

$^1$H NMR (CDCl$_3$, 500 MHz): 7.72 (d, J=7.5 Hz, 2H), 7.66 (d, J=8.5 Hz, 2H), 7.58 (d, J=7.5 Hz, 2H), 7.51 (d, J=7.5 Hz, 2H), 7.14 (t, J=7.5 Hz, 2H), 6.98 (d, J=3.5 Hz, 2H), 6.74 (d, J=3.5 Hz, 2H), 2.80-2.85 (dd, J=14.5 Hz, J=6.5 Hz, 2H), 2.61-2.67 (dd, J=14.5 Hz, J=8.0 Hz, 2H), 1.64-1.72 (m, br, 2H), 1.44-1.54 (m, br, 2H), 1.19-1.30 (m, br, 2H), 0.92-0.97 (m, br, 12H).

Preparation of (S)-2MB-Thienocoronene

A solution of 1,7(or 1,6)-bis[5-((s)-2-methylbutyl)thiophen-2-yl]perylene (0.14 g, 0.25 mmol), iodine (0.14 g, 0.55 mmol), and benzene (180 mL) was sonicated for 5 minutes, and placed in a UV-reactor for 15 hours. The reaction mixture was washed with saturated Na$_2$SO$_3$ aqueous solution and water, dried over anhydrous Na$_2$SO$_4$, and concentrated in vacuo. The residue was subjected to flash column chromatography on silica gel with a chloroform:hexane (1:4, v/v) mixture as the eluent, leading to a slightly yellow solid as the product (97.2 mg, 69.9%).

$^1$H NMR (CDCl$_3$, 500 MHz): 8.99 (d, J=8.5 Hz, 2H), 8.79 (d, J=8.5 Hz, 2H), 8.69 (d, J=8.5 Hz, 2H), 8.67 (d, J=8.5 Hz, 2H), 8.17 (s, 2H), 3.27-3.31 (dd, J=14.5 Hz, J=6.0 Hz, 2H), 3.07-3.12 (dd, J=14.5 Hz, J=8.0 Hz, 2H), 2.08 (m, br, 2H), 1.72 (m, br, 2H), 1.45 (m, br, 2H), 1.17 (d, J=6.5 Hz, 6H), 1.07-1.11 (t, J=7.0 Hz, 6H). Elemental Analysis (calc. C, 82.56; H, 5.83; N, 0.00). found C, 82.51; H, 5.89; N, 0.00.

EXAMPLE 5

Synthesis of undecanoxy-thienocoronene

Preparation of 2-undecanoxy-thiophene

A mixture of 2-methoxythiophene (5.13 g, 44.93 mmol), n-C$_{11}$H$_{23}$OH (15.5 g, 89.87 mmol), toluene (50 mL), and p-toluenesulfonic acid monohydrate (0.85 g, 4.47 mmol) was heated to reflux under nitrogen for 19 hours. After cooling to room temperature, the reaction mixture was poured into water (150 mL), and the mixture was extracted with dichloromethane (DCM, 250 mL). The organic layer was washed with water and brine, dried over Na$_2$SO$_4$, and concentrated in vacuo. The residue was subjected to flash column on silica gel with hexane as eluent (slowly up to a hexane:DCM (8:2, v/v) mixture), leading to a colorless oil as the product (7.76 g, 67.9%).

$^1$H NMR (CDCl$_3$, 500 MHz): 6.71 (dd, J=5.5, J=4.0 Hz, 1H), 6.54 (dd, J=5.5 Hz, J=1.5 Hz, 1H), 6.20 (dd, J=4.0 Hz, J=1.5 Hz, 1H), 4.03 (t, J=6.5 Hz, 2H), 1.78 (m, 2H), 1.44 (m, 2H), 1.24-1.36 (m, br, 16H), 0.89 (t, J=7.0, 3H).

Preparation of 2-undecanoxy-5-trimethystannylthiophene

A solution of 2-undecanoxy-thiophene (4.23 g, 16.6 mmol) in dry THF (80 mL) was cooled to −78° C., and a solution of n-BuLi (2.5 M, 10 mL, 25.0 mmol) was then added slowly. This mixture was stirred at −78° C. for additional 10 minutes, and then allowed to warm to room temperature and stirred at room temperature for 30 minutes, before it was cooled back to −78° C. A solution of trimethylstannyl chloride (1.0 M, 25 mL, 25.0 mmol) was added slowly. This mixture was stirred at −78° C. for 2 hours, and then allowed to warm to room temperature, and stirred at room temperature overnight. The reaction was quenched by water (20 mL), and the reaction mixture was diluted with hexane (250 mL), washed with water (100 mL×2), dried over Na$_2$SO$_4$, and concentrated on a rotary evaporator, leading to a slightly yellow oil (6.94 g, 100.0%), which was directly used in the next step without further purification.

$^1$H NMR (CDCl$_3$, 500 MHz): 6.81 (d, J=3.5 Hz, 1H), 6.33 (d, J=3.5 Hz, 1H), 4.03 (t, J=6.5 Hz, 2H), 1.78 (m, 2H), 1.44 (m, 2H), 1.25-1.35 (m, br, 16H), 0.89 (t, J=7.0, 3H), 0.33 (s, 9H).

Preparation of 1,7(or 1,6)-bis[5-undecanoxythiophen-2-yl]perylene-3,4:9,10-tetracarboxylic dianhydride A mixture of PDA-Br$_2$ (2.29 g, 4.16 mmol), 2-undecanoxy-5-trimethystannylthiophene (6.94 g, 16.6 mmol), Pd(PPh$_3$)$_4$ (0.4 g, 0.35 mmol) in dry toluene (80 mL) was heated at reflux for 40 hours under argon. After cooling to room temperature, a HCl solution (2M, 20 mL) was added, and the resulting mixture was stirred at room temperature for 30 minutes. The reaction mixture was diluted with chloroform (200 mL), and this mixture was washed with water (150 mL×2), dried over Na$_2$SO$_4$, and passed through a short pad of silica gel. The filtrate was concentrated in vacuo, and the residue was treated with hexane, leading to a dark solid as the product, which was used directly in the next step without further purification (3.41 g, 91.4%).

$^1$H NMR (CDCl$_3$, 400 MHz): 8.67 (s, 2H), 8.40 (d, J=8.0 Hz, 2H), 8.33 (d, J=8.0 Hz, 2H), 7.05 (d, J=4.0 Hz, 2H), 6.28 (d, J=4.0 Hz, 2H), 4.09 (t, J=6.4 Hz, 4H), 1.84 (m, 4H), 1.447 (m, 4H), 1.23-1.41 (m, br, 32H), 0.89 (t, J=6.8, 6H).

Preparation of 1,7(or 1,6)-bis[5-undecanoxythiophen-2-yl]perylene

A mixture of 1,7(or 1,6)-bis[5-undecanoxythiophen-2-yl]perylene-3,4:9,10-tetracarboxylic dianhydride (0.918 g, 1.02 mmol), Cu$_2$O (0.72 g, 5.03 mmol), bipyridyl (0.39 g, 2.50 mmol), water (2.6 mL), and quinoline (20 mL) was stirred at reflux temperature under nitrogen for 40 hours. Upon cooling to room temperature, the reaction mixture was diluted with chloroform (250 mL), and the resulting mixture was washed with HCl (2M, 150 mL×2), water (150 mL), dried over Na$_2$SO$_4$, and concentrated in vacuo. The residue was subjected to column chromatography on silica gel with a chloroform:hexane (3:7, v/v) mixture, leading to a sticky orange solid (0.38 g, 49.4%), which was directly used in the next step without further purification.

$^1$H NMR (CDCl$_3$, 500 MHz): 7.88 (d, J=7.5 Hz, 2H), 7.65 (d, J=8.0 Hz, 2H), 7.58 (d, J=8.0 Hz, 2H), 7.48 (d, J=8.0 Hz, 2H), 7.24 (t, J=8.0 Hz, 2H), 6.80 (d, J=4.0 Hz, 2H), 6.18 (d, J=4.0 Hz, 2H), 4.05 (t, J=6.5 Hz, 4H), 1.80 (m, br, 4H), 1.45 (m, br, 4H), 1.23-1.40 (m, br, 28H), 0.89 (t, J=7.0 Hz, 6H).

Preparation of undecanoxy-thienocoronene

A solution of 1,7(or 1,6)-bis[5-undecanoxythiophen-2-yl]perylene (0.38 g, 0.50 mmol), iodine (0.34 g, 1.34 mmol), propylene oxide (35 mL), and benzene (300 mL) was sonicated for 5 minutes, and placed in a UV-reactor for 15.5 hours. Precipitation of a slightly yellow/greenish yellow compound was observed. The precipitate was collected by filtration, washed thoroughly with hexane and methanol, and dried in vacuum, leading to a slightly yellow solid as the product (250 mg, 66.1%).

MP: 215-217° C. Elemental Analysis (calc. C, 79.74; H, 7.49; N, 0.00). found C, 79.82; H, 7.60; N, 0.00.

EXAMPLE 6

Synthesis of dodecyl-thienocoronene

Preparation of 2-dodecylthiophene

A solution of thiophene (14.3 g, 0.17 mol) in dry THF (150 mL) was cooled to −78° C. under nitrogen. A solution of n-BuLi (38.0 mL, 2.5 M, 95.0 mmol) was then added dropwise over a course of 40 minutes. After addition, the reaction mixture was stirred at −78° C. for additional 2 hours, before a solution of n-C$_{12}$H$_{25}$Br (16.9 g, 67.8 mmol) in dry THF (25 mL) was added slowly. This mixture was stirred at −78° C. for 1 hour, and then allowed to warm to room temperature slowly and stirred at room temperature overnight. The reaction was quenched by water (20 mL) and the mixture was poured into water (400 mL), and the resulting mixture was extracted with ether (400 mL). The organic layer was washed with water and brine, dried over MgSO$_4$, and concentrated on a rotary evaporator. The residue was subjected to column chromatography on silica gel with hexane as eluent, leading to a colorless oil as the product. (8.68 g, 50.7%)

$^1$H NMR (CDCl$_3$, 500 MHz): 7.11 (dd, J=5.0 Hz, J=1.0 Hz, 1H), 6.92 (d, J=5.0 Hz, J=3.5 Hz, 1H), 6.78 (dd, J=3.5 Hz, J=1.0 Hz, 1H), 2.82 (t, J=7.5 Hz, 2H), 1.68 (m, 2H), 1.23-1.40 (m, br, 18H), 0.89 (t, J=7.0, 3H).

Preparation of 5-dodecyl-2-trimethylstannylthiophene

A solution of 2-dodecylthiophene (5.18 g, 20.5 mmol) in dry THF (90 mL) was cooled to −78° C., and a solution of n-BuLi (2.5 M, 12.3 mL, 30.8 mmol) was then added slowly. This mixture was stirred at −78° C. for additiona 10 minutes, and then allowed to warm to room temperature and stirred at room temperature for 30 minutes, before it was cooled back to −78° C. A solution of trimethylstannyl chloride (1.0 M, 31 mL, 31.0 mmol) was added slowly. This mixture was stirred at −78° C. for 2 hours, and then allowed to warm to room temperature, and stirred at room temperature overnight. The reaction was quenched by water (20 mL), and the reaction mixture was diluted with hexane (200 mL), washed with water, dried over Na$_2$SO$_4$, and concentrated on a rotary evaporator, leading to a slightly yellow oil (8.35 g, 98.0%), which was directly used in the next step without further purification.

$^1$H NMR (CDCl$_3$, 500 MHz): 7.02 (d, J=3.5 Hz, 1H), 6.91 (d, J=3.0 Hz, 1H), 2.86 (t, J=7.5 Hz, 2H), 1.68 (m, 2H), 1.23-1.41 (m, br, 18H), 0.89 (t, J=7.5 Hz, 3H), 0.35 (s, 9H).

Preparation of 1,7(or 1,6)-bis[5-dodecylthiophen-2-yl]perylene-3,4:9,10-tetracarboxylic dianhydride A mixture of PDA-Br$_2$ (2.77 g, 5.03 mmol), 5-dodecyl-2-trimethylstannylthiophene (8.35 g, 20.1 mmol), Pd(PPh$_3$)$_4$ (0.58 g, 0.50 mmol) in dry toluene (100 mL) was heated at reflux for 40 hours under argon. After cooling to room temperature, a HCl solution (2M, 20 mL) was added, and the resulting mixture was stirred at room temperature for 30 minutes. The reaction mixture was diluted with chloroform (250 mL), and this mixture was washed with water (150 mL×2), dried over Na$_2$SO$_4$, and passed through a short pad of silica gel. The filtrate was concentrated in vacuo, leading to a dark solid as the product, which was used directly in the next step without further purification (4.1 g, 91.1%).

$^1$H NMR (CDCl$_3$, 500 MHz): 8.69 (s, 2H), 8.28 (s, 4H), 7.16 (d, J=3.5 Hz, 2H), 6.87 (d, J=3.5 Hz, 2H), 2.89 (t, J=7.5 Hz, 4H), 1.72 (m, 4H), 1.24-1.45 (m, br, 36H), 0.88 (t, J=7.0 Hz, 6H). Minor peaks: 8.67 (s), 8.29 (d, J=8.5 Hz), 8.23 (d, J=8.5 Hz), 7.04 (d, J=3.5 Hz), 6.85 (d, J=3.5 Hz).

Preparation of 1,7(or 1,6)-bis[5-dodecylthiophen-2-yl]perylene

A mixture of 1,7(or 1,6)-bis[5-dodecylthiophen-2-yl]perylene-3,4:9,10-tetracarboxylic dianhydride (1.80 g, 2.02 mmol), Cu$_2$O (1.43 g, 9.99 mmol), bipyridyl (0.78 g, 4.99 mmol), water (6.5 mL), and quinoline (40 mL) was stirred at reflux temperature under nitrogen for 39 hours. The reaction mixture was cooled to room temperature, diluted with chloroform (200 mL), washed with HCl (2M, 200 mL×2) then water (200 mL), dried over Na$_2$SO$_4$, and concentrated in vacuo. The residue was subjected to column chromatography on silica gel with a chloroform:hexane (2:8, v/v) mixture, leading to an orange solid (1.00 g, 65.8%).

$^1$H NMR (CDCl$_3$, 500 MHz): 7.75 (d, J=7.5 Hz, 2H), 7.66 (d, J=8.5 Hz, 2H), 7.58 (d, J=7.5 Hz, 2H), 7.50 (d, J=8.5 Hz, 2H), 7.16 (t, J=7.5 Hz, 2H), 6.97 (d, J=3.5 Hz, 2H), 6.75 (d, J=3.5 Hz, 2H), 2.84 (m, 4H), 1.69 (m, br, 4H), 1.25-1.44 (m, br, 36H), 0.89 (t, J=7.0 Hz, 6H).

Preparation of dodecyl-thienocoronene

A solution of 1,7(or 1,6)-bis[5-dodecylthiophen-2-yl]perylene (0.81 g, 1.07 mmol), iodine (0.62 g, 2.44 mmol), and benzene (550 mL) was sonicated for 5 minutes, and placed in a UV-reactor for 16 hours. Precipitation of a slightly yellow solid was observed, and the solid was collected by filtration, washed with hexane, and dried in vacuum (0.57 g, 70.7%).

Elemental Analysis (calc. C, 83.37; H, 8.07; N, 0.00). found C, 83.37; H, 8.17; N, 0.00.

EXAMPLE 7

Synthesis of (S)-2MB-furocoronene

Preparation of (S)-2-(2-methylbutyl)furan

A solution of furan (8.16 g, 0.13 mol) in dry THF (100 mL) was cooled to −78° C. under nitrogen. A solution of n-BuLi (28.0 mL, 2.5 M, 70.0 mmol) was then added dropwise. After addition, the reaction mixture was stirred at −78° C. for additional 1 hour, before a solution of (S)-2-methylbutyliodide (10.0 g, 50.5 mmol) in dry THF (20 mL) was added slowly. This mixture was stirred at −78° C. for 2 hours, and then allowed to warm to room temperature slowly and stirred at room temperature overnight. The reaction was quenched by water (20 mL) and the mixture was poured into water (200 mL), and the resulting mixture was extracted with ether (300 mL). The organic layer was washed with water and brine, dried over $Na_2SO_4$, and concentrated on a rotary evaporator. The residue was subjected to column chromatography on silica gel with hexane as eluent, leading to a colorless oil as the product. (6.18 g, 88.5%).

$^1$H NMR ($CDCl_3$, 500 MHz): 7.31 (dd, J=2.0 Hz, J=1.0 Hz, 1H), 6.29 (dd, J=3.0 Hz, J=2.0 Hz, 1H), 5.98 (dd, J=3.0 Hz, J=1.0 Hz, 1H), 2.59-2.65 (dd, J=14.5 Hz, J=7.0 Hz, 1H), 2.41-2.47 (dd, J=14.5 Hz, J=7.5 Hz, 1H), 1.82-1.93 (m, 1H), 1.46-1.54 (m, 1H), 1.00-1.10 (m, 1H), 0.97 (d, J=6.5 Hz, 3H), 0.89 (t, J=7.0 Hz, 3H).

Preparation of
(S)-2-(2-methylbutyl)-5-trimethylstannylfuran

A solution of (S)-2-(2-methylbutyl)furan (4.10 g, 29.7 mmol) in dry THF (100 mL) was cooled to −78° C., and a solution of n-BuLi (2.5 M, 18.0 mL, 45.0 mmol) was then added slowly. This mixture was stirred at −78° C. for additional 20 minutes, and then allowed to warm to room temperature and stirred at room temperature for 60 minutes, before it was cooled back to −78° C. A solution of trimethylstannyl chloride (1.0 M, 45 mL, 45.0 mmol) was added slowly. This mixture was stirred at −78° C. for 1 hour, and then allowed to warm to room temperature, and stirred at room temperature overnight. The reaction was quenched by water (20 mL), and reaction mixture was diluted with hexane (300 mL), washed with water (200 mL×2), dried over $Na_2SO_4$, and concentrated on a rotary evaporator, leading to a slightly yellow oil (7.43 g, 83.2%).

$^1$H NMR ($CDCl_3$, 500 MHz): 6.49 (d, J=3.0 Hz, 1H), 6.00 (d, J=3.0 Hz, 1H), 2.62-2.68 (dd, J=14.5 Hz, J=6.0 Hz, 1H), 2.45-2.52 (dd, J=14.5 Hz, J=7.5 Hz, 1H), 1.60-1.72 (m, 1H), 1.45-1.54 (m, 1H), 1.14-1.23 (m, 1H), 0.88-0.93 (m, br, 6H). 0.31 (s, 9H).

Preparation of 1,7(or 1,6)-bis[5-((s)-2-methylbutyl)furyl]perylene-3,4:9,10-tetracarboxylic dianhydride A mixture of PDA-$Br_2$ (3.40 g, 6.20 mmol), (S)-2-(2-methylbutyl)-5-trimethylstannylfuran (7.43 g, 24.7 mmol), $Pd(PPh_3)_4$ (0.71 g, 0.61 mmol) in dry toluene (120 mL) was heated at reflux for 41 hours under argon. After cooling to room temperature, a HCl solution (2M, 20 mL) was added, and the resulting mixture was stirred at room temperature for 30 minutes. The reaction mixture was diluted with chloroform (300 mL), and this mixture was washed with water (200 mL×2), dried over $Na_2SO_4$, passed through a short pad of silica gel. The filtrate was concentrated in vacuo, and the residue was treated with hexane, leading to a dark solid as the product, which was used directly in the next step without further purification (2.11 g, 53.0%).

$^1$H NMR ($CDCl_3$, 500 MHz): 8.78 (s, 2H), 8.38 (d, J=8.0 Hz, 2H), 7.59 (d, J=8.0 Hz, 2H), 6.95 (d, J=3.0 Hz, 2H), 6.35 (d, J=3.0 Hz, 2H), 2.50-2.55 (dd, J=14.5 Hz, J=6.5 Hz, 2H), 2.32-2.39 (dd, J=15.0 Hz, J=8.0 Hz, 2H), 1.42-1.50 (m, br, 2H), 1.32-1.40 (m, br, 2H), 1.08-1.19 (m, br, 2H), 0.82-0.90 (m, br, 12H).

Preparation of 1,7(or 1,6)-bis[5-((s)-2-methylbutyl)furyl]perylene

A mixture of 1,7(or 1,6)-bis[5-((s)-2-methylbutyl)furyl]perylene-3,4:9,10-tetracarboxylic dianhydride (1.03 g, 1.55 mmol), $Cu_2O$ (1.10 g, 7.69 mmol), bipyridyl (0.60 g, 3.84 mmol), water (4.0 mL), and quinoline (30 mL) was stirred at reflux under nitrogen for 46 hours. After cooling to room temperature, the reaction mixture was diluted with chloroform (250 mL), washed with HCl (2M, 200 mL×2) and water (200 mL), dried over $Na_2SO_4$, and the solvent was removed in vacuo. The residue was subjected to column chromatography on silica gel with a chloroform:hexane (2:8, slowly up to 3:8, v/v, flash) mixture, leading to an orange solid (0.65 g, 80.0%), which was directly used in the next step without further purification.

$^1$H NMR ($CDCl_3$, 500 MHz): 7.70 (d, J=8.5 Hz, 2H), 7.61 (m, 2H), 7.55 (d, J=8.0 Hz, 2H), 7.23 (m, 4H), 6.54 (d, J=3.0 Hz, 2H), 6.16 (d, J=3.5 Hz, 2H), 2.46-2.55 (dd, J=15.0 Hz, J=6.0 Hz, 2H), 2.30-2.36 (dd, J=15.0 Hz, J=8.0 Hz, 2H), 1.50-1.60 (m, br, 2H), 1.33-1.42 (m, br, 2H), 1.08-1.17 (m, br, 2H), 0.82-0.91 (m, br, 12H).

Preparation of (S)-2MB-Furocoronene

A solution of 1,7(or 1,6)-bis[5-((s)-2-methylbutyl)furyl]perylene (0.63 g, 1.20 mmol), iodine (0.69 g, 2.72 mmol), and benzene (620 mL) was sonicated for 5 minutes, and placed in a UV-reactor for 17 hours. The reaction mixture was washed with saturated $Na_2SO_3$ aqueous solution and water, dried over anhydrous $Na_2SO_4$, and concentrated in vacuo. The residue was subjected to flash column chromatography on silica gel with a chloroform:hexane (1:4, v/v, slowly up to 3:8) mixture as eluent, leading to a slightly yellow solid as the product (245 mg, 39.2%).

$^1$H NMR ($CDCl_3$, 500 MHz): 9.20 (d, J=8.5 Hz, 2H), 8.99 (d, J=8.5 Hz, 2H), 8.88 (d, J=9.0 Hz, 2H), 8.86 (d, J=9.0 Hz, 2H), 7.49 (s, 2H), 3.18-3.24 (dd, J=15.0 Hz, J=6.5 Hz, 2H), 2.99-3.06 (dd, J=15.0 Hz, J=8.0 Hz, 2H), 2.18-2.27 (m, br, 2H), 1.63-1.74 (m, br, 2H), 1.40-1.50 (m, br, 2H), 1.17 (d, J=6.5 Hz, 6H), 1.07-1.12 (t, J=7.5 Hz, 6H). Elemental Analysis (calc. C, 87.66; H, 6.19; N, 0.00). found C, 87.38; H, 5.97; N, 0.00.

EXAMPLE 8

Device Fabrication and Test Procedures

Device Fabrication Procedure (Bottom Gate Top Contact (BGTC)): BGTC thin film field-effect transistors (FET) were fabricated using compounds of the present teachings as the semiconductor layer. N-doped silicon wafers (100) with 3000 Å thermally grown silicon dioxide layer (Addison Inc.) were used as the device substrates. Prior to deposition of the semiconductor, the $Si/SiO_2$ surfaces were modified through a special octadecyltrichlorosilane (OTS) treatment process. Thin films of semiconductors, approximately 40-120 nm in thickness, were prepared through physical vapor deposition, with a deposition rate of about 0.1-0.5 Å/s and a substrate temperature of about 30-120° C. The TFTs were completed by vapor deposition of 300 Å gold source/drain electrodes onto the semiconductor layer through a stencil mask to define the transistor channel. The channel lengths and widths are about 50-200 μm and about 500-2000 μm, respectively. The silicon dioxide layer served as the gate insulator. The gate electrode was accessed through an ohmic contact to the doped silicon.

Device Fabrication Procedure (Top Gate Bottom Contact (TGBC)): For TGBC FET devices, glass substrates (1"×1", PGO) were planarized with UV-curable polymeric films (ActivInk D1400, Polyera Corp., Skokie, Ill.). Au source and drain electrodes were thermally evaporated through a stencil onto these substrates. The semiconductor was spun from a DCB solution (10 mg-mL) at 1500 rpm to yield a film with a thickness of about 20-30 nm. These films were then baked overnight in a vacuum oven at 110° C. to remove any residual solvent. The amorphous fluoropolymer CYTOP™ (CTL-809M, Asahi Glass Corporation) was spun as the top-gate dielectric at 5000 rpm to a thickness of about nm, and baked in a vacuum oven at about 110° C. for 1 hour. The device structure was completed by the evaporation of an aligned Au top-gate stripe.

Device Fabrication Procedure (Bottom Gate Bottom Contact (BGBC)): For BGBC FET devices, a Cr/Au gate stripe was evaporated on clean glass substrates. Subsequently, UV-curable polymeric films (ActivInk D1450, Polyera Corp., Skokie, Ill.) were spun (thickness ~500 nm) and cured to form the bottom-gate dielectric, Au source drain electrodes and thin films of the semiconductor were prepared according to the same protocols as for the TGBC devices.

All FET devices were characterized in a Signatone Probe Station using a Keithley 4200 Semiconductor Characterization System to obtain transfer and output characteristics. FET performance parameters were extracted from the transfer characteristics according to standard transistor equations.

Figure 2:
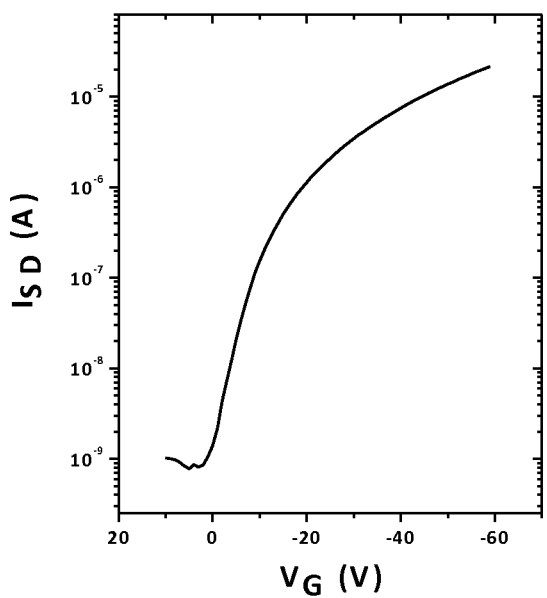
FIG. 2 shows a representative transfer plot of a top gate bottom contact device incorporating a solution-processed semiconductor film prepared from a compound of the present teachings.

FIG. 2 shows a representative transfer plot of a top gate bottom contact device incorporating a solution-processed semiconductor film prepared from a compound of the present teachings.

Figure 3:
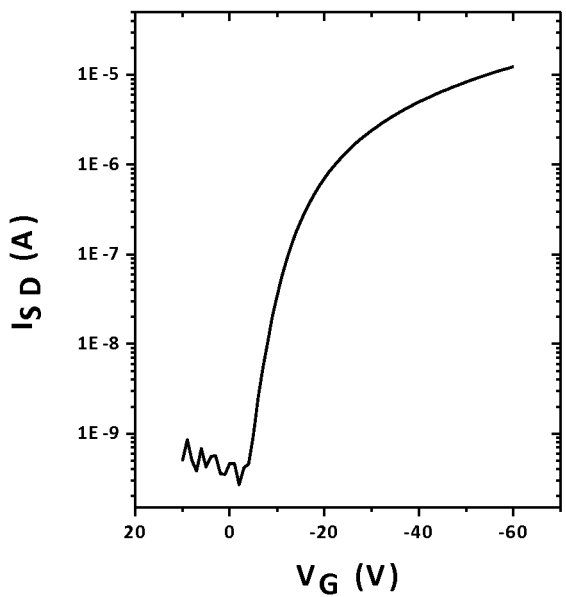
FIG. 3 shows a representative transfer plot of a bottom gate bottom contact device incorporating a solution-processed semiconductor film prepared from a compound of the present teachings.

FIG. 3 shows a representative transfer plot of a bottom gate bottom contact device incorporating a solution-processed semiconductor film prepared from a compound of the present teachings.

The performance parameters of various FET devices according to the present teachings are reported in Table 1 below.

TABLE 1

| Compound | Device Configuration | Mobility (cm$^2$/Vs) | $I_{on}/I_{off}$ | $V_{on}$ (V) |
|---|---|---|---|---|
| 1MP-thienocoronene | TGBC | 0.10~1.50 | 3~6 | −20~0 |
|  | BGBC | 0.01~0.50 | 3~6 | −15~−1 |
| (s)-2MB-thienocoronene | TGBC | 0.10~1.50 | 4~6 | −20~−1 |
| 1PB-thienocoronene | TGBC | 0.02~0.50 | 1~2 | −38~−20 |
| 2BO-thienocoronene | TGBC | 0.004~0.01 | 1~2 | −20~−2 |
| (s)-2MB-furocoronene | TGBC | 0.002~0.01 | 3~5 | −19~−8 |

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound having formula I:

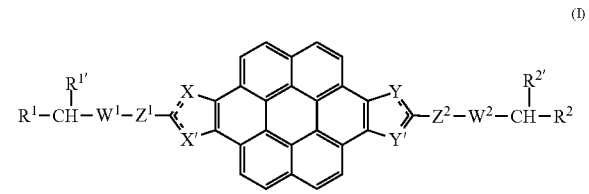

wherein:

$W^1$ and $W^2$ independently are —$(CR^cR^d)_m$— or —$(SiR^eR^f)$—;

X and X' are selected from the group consisting of S, O, $NR^a$ and $CR^b$, provided that one of X and X' is selected from the group consisting of S, O, and $NR^a$, and the other X and X' is $CR^b$;

Y and Y' are selected from the group consisting of S, O, $NR^{a'}$ and $CR^{b'}$, provided that one of Y and Y' is selected from the group consisting of S, O, and $NR^{a'}$, and the other Y and Y' is $CR^{b'}$;

$Z^1$ and $Z^2$ independently are selected from the group consisting of O, S, —C≡C—, and a covalent bond;

$R^a$ and $R^{a'}$ independently are selected from the group consisting of H, a $C_{1-20}$ alkyl group, a $C_{2-20}$ alkenyl group, and a $C_{1-20}$ haloalkyl group;

$R^b$ and $R^{b'}$ independently are selected from the group consisting of H, a $C_{1-20}$ alkyl group, a $C_{2-20}$ alkenyl group, and a $C_{1-20}$ haloalkyl group;

$R^c$ and $R^d$ independently are selected from the group consisting of H, a $C_{1-20}$ alkyl group, and a $C_{1-20}$ haloalkyl group;

$R^e$ and $R^f$ independently are selected from the group consisting of H, a $C_{1-20}$ alkyl group, and a $C_{1-20}$ haloalkyl group;

$R^1$, $R^{1'}$, $R^2$, and $R^{2'}$ independently are selected from the group consisting of a linear $C_{1-40}$ alkyl group, a linear $C_{2-40}$ alkenyl group, and a linear $C_{1-40}$ haloalkyl group; and m, at each occurrence, independently is 0, 1, 2, 3, or 4.

2. The compound of claim 1, wherein the compound has the formula IIa or IIIa:

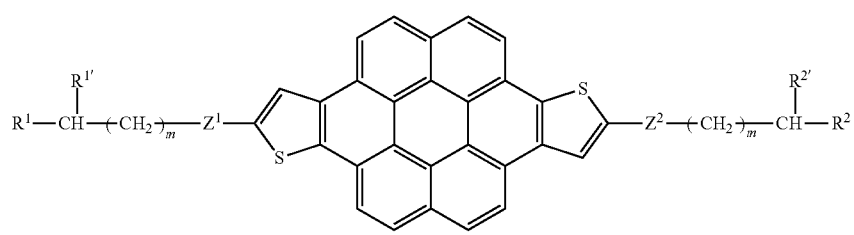

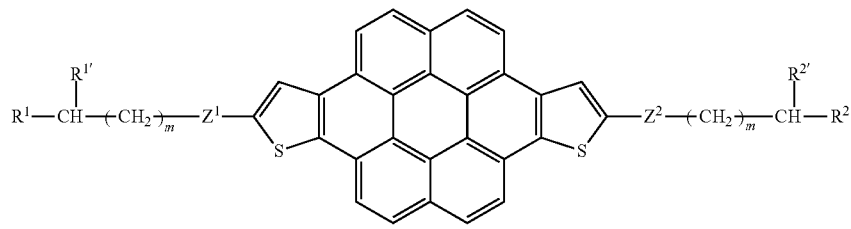

(IIIa)

wherein $R^1$, $R^{1'}$, $R^2$, $R^{2'}$, $Z^1$, $Z^2$, and m are as defined in claim 1.

3. The compound of claim 1, wherein the compound has the formula IVa or Va:

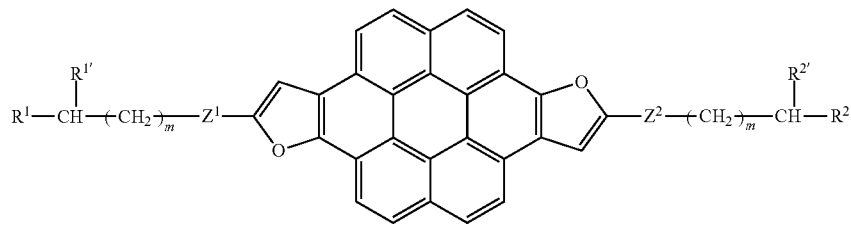

(IVa)

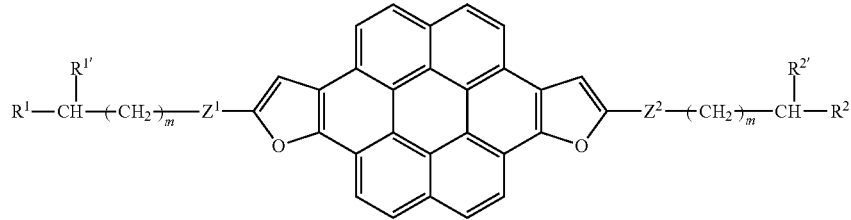

(Va)

wherein $R^1$, $R^{1'}$, $R^2$, $R^{2'}$, $Z^1$, $Z^2$, and m are as defined in claim 1.

4. The compound of claim 2, wherein $Z^1$ and $Z^2$ independently are O or a covalent bond.

5. The compound of claim 2, wherein each m independently is 0, 1, or 2.

6. The compound of claim 2, wherein $R^1$ and $R^2$ independently are selected from the group consisting of a linear $C_{3-40}$ alkyl group, a linear $C_{4-40}$ alkenyl group, and a linear $C_{3-40}$ haloalkyl group; and $R^{1'}$ and $R^{2'}$ independently are selected from the group consisting of $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$.

7. The compound of claim 1, wherein the compound has the formula IIb or IIIb:

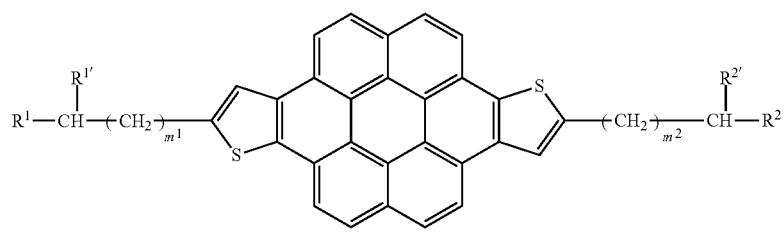

(IIb)

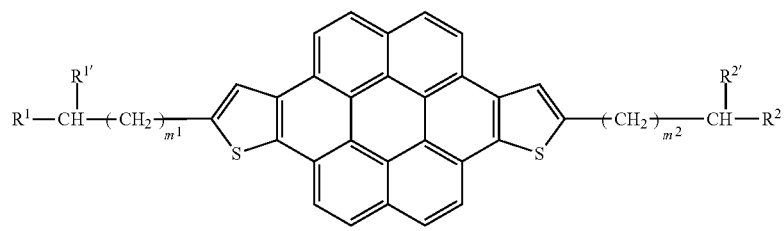

(IIIb)

wherein R[1] and R[2] independently are selected from the group consisting of a linear $C_{3-40}$ alkyl group, a linear $C_{4-40}$ alkenyl group, and a linear $C_{3-40}$ haloalkyl group; R[1'] and R[2'] independently are selected from the group consisting of $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$; and $m^1$ and $m^2$ independently are 0, 1, or 2.

8. The compound of claim 1, wherein the compound has the formula IVb or Vb:

9. The compound of claim 1, wherein the compound has the formula IIc, IIIc, IVc, or Vc:

wherein R[1] and R[2] independently are selected from the group consisting of a linear $C_{3-40}$ alkyl group, a linear $C_{4-40}$ alkenyl group, and a linear $C_{3-40}$ haloalkyl group; R[1'] and R[2'] independently are selected from the group consisting of $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$; and $m^1$ and $m^2$ independently are 0, 1, or 2.

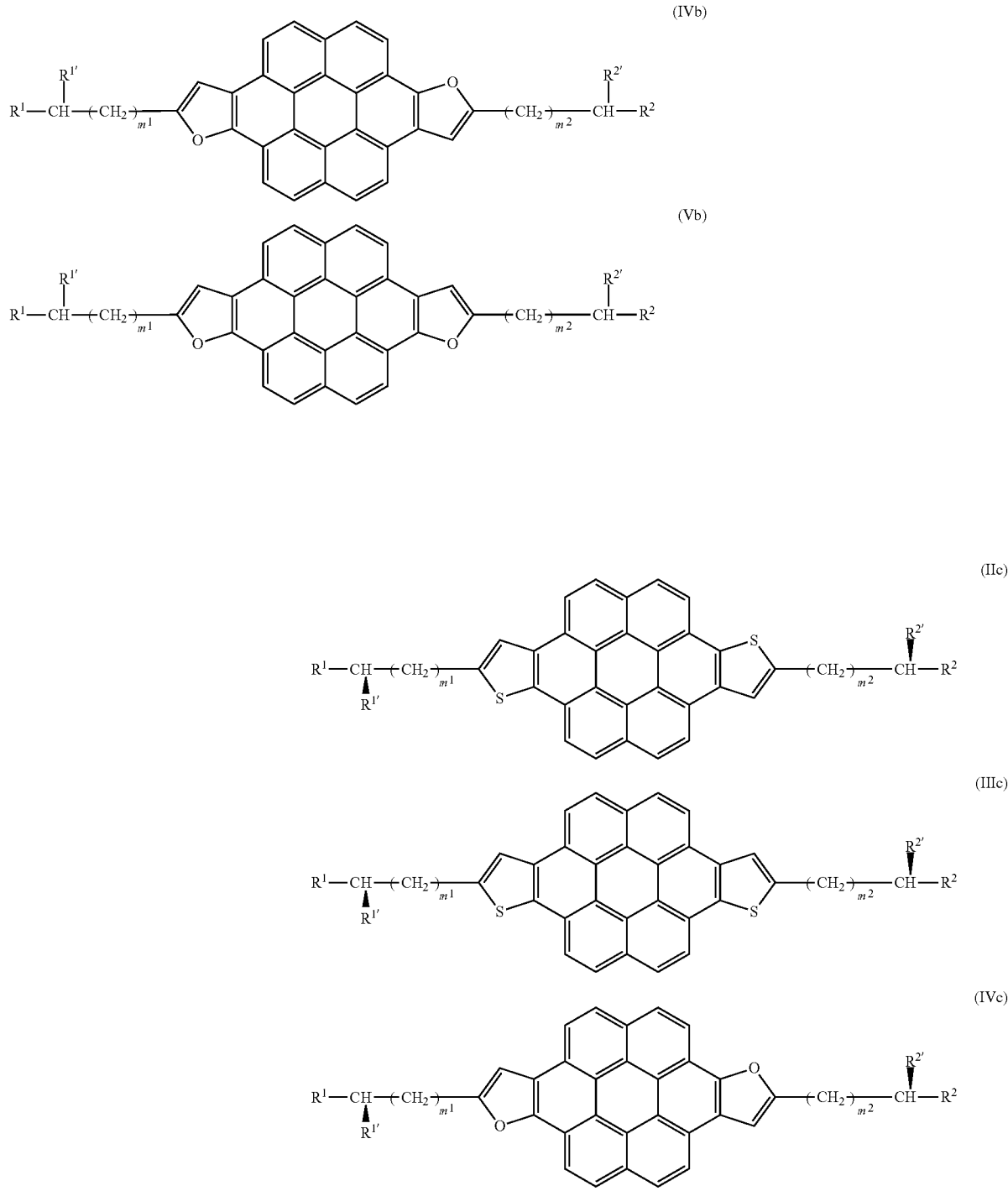

-continued (Vc)
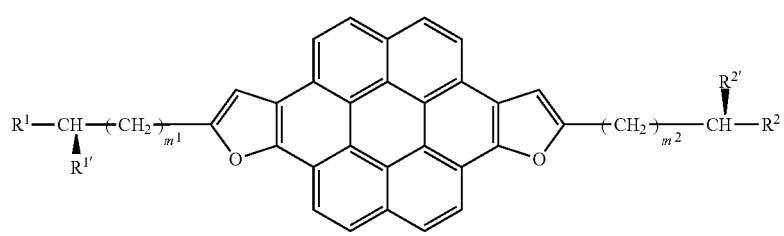

wherein $R^1$ and $R^2$ independently are selected from the group consisting of a linear $C_{3-40}$ alkyl group, a linear $C_{4-40}$ alkenyl group, and a linear $C_{3-40}$ haloalkyl group; $R^{1\prime}$ and $R^{2\prime}$ independently are selected from the group consisting of $CH_3$, $CF_3$, $C_2H_5$, $C_2F_5$, $CH_2CF_3$, $CF_2CH_3$, $CH_2CH_2CH_3$, $CF_2CF_2CF_3$, $CH_2CH_2CF_3$, $CH_2CH_2CH_2CH_3$, $CF_2CF_2CF_2CF_3$, and $CH_2CH_2CH_2CF_3$; and $m^1$ and $m^2$ independently are 0, 1, or 2.

10. A compound having formula VI:

(VI)
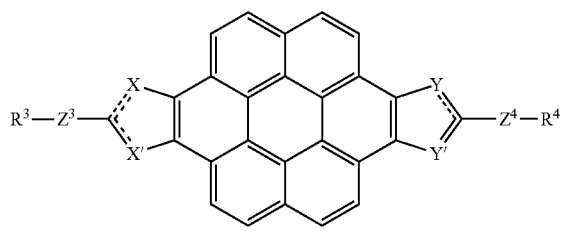

wherein:

X and X' are selected from the group consisting of S, O, $NR^a$ and $CR^b$, provided that one of X and X' is selected from the group consisting of S, O, and $NR^a$, and the other X and X' is $CR^b$;

Y and Y' are selected from the group consisting of S, O, $NR^{a\prime}$ and $CR^{b\prime}$, provided that one of Y and Y' is selected from the group consisting of S, O, and $NR^{a\prime}$, and the other Y and Y' is $CR^{b\prime}$;

$Z^3$ and $Z^4$ independently are selected from the group consisting of O, S, and —C≡C—;

$R^a$ and $R^{a\prime}$ independently are selected from the group consisting of H, a $C_{1-20}$ alkyl group, a $C_{2-20}$ alkenyl group, and a $C_{1-20}$ haloalkyl group;

$R^b$ and $R^{b\prime}$ independently are selected from the group consisting of H, a $C_{1-20}$ alkyl group, a $C_{2-20}$ alkenyl group, and a $C_{1-20}$ haloalkyl group; and $R^3$ and $R^4$ independently are selected from the group consisting of a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group, and a $Si(C_{1-40}$ alkyl$)_3$ group.

11. The compound of claim 10, wherein the compound has the formula VII or VIII:

(VII)
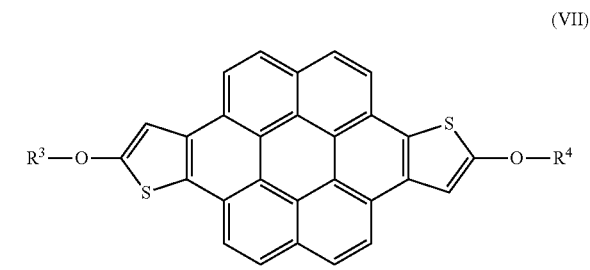

(VIII)
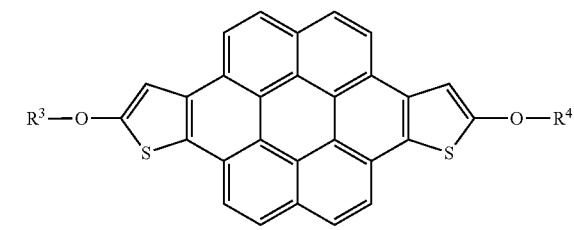

wherein $R^3$ and $R^4$ are as defined in claim 10.

12. A compound having formula IX, X, XI, or XII:

(IX)
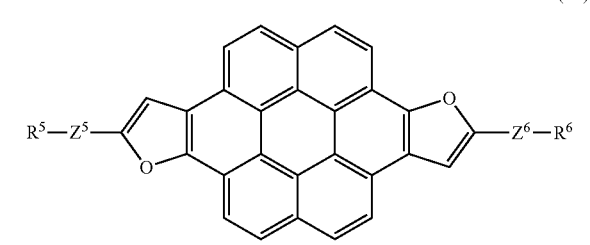

(X)
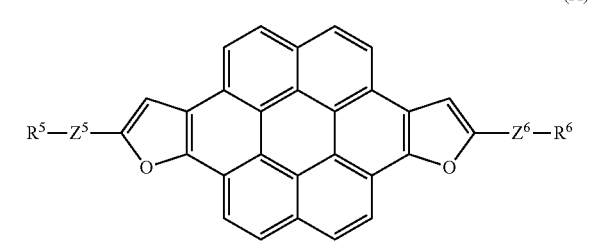

-continued

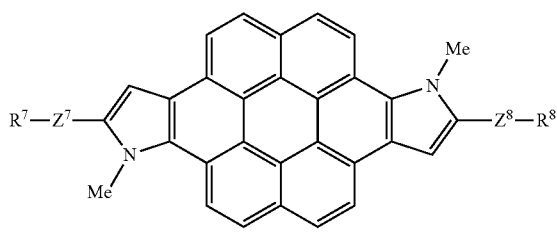
(XI)

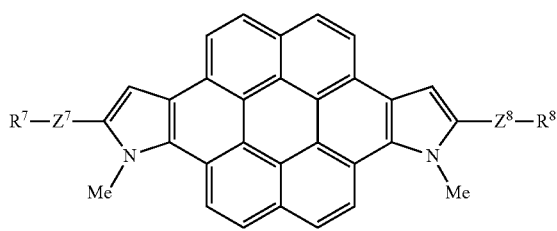
(XII)

wherein:

$Z^5$ and $Z^6$ independently are selected from the group consisting of O, S, —C≡C—, and a covalent bond;

$Z^7$ and $Z^8$ independently are selected from the group consisting of O, S, —C≡C—, and a covalent bond;

$R^5$ and $R^6$ independently are selected from the group consisting of a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group, and a $Si(C_{1-40}$ alkyl$)_3$ group; and $R^7$ and $R^8$ independently are selected from the group consisting of a linear or branched $C_{1-40}$ alkyl group, a linear or branched $C_{2-40}$ alkenyl group, a linear or branched $C_{2-40}$ alkynyl group, a linear or branched $C_{1-40}$ haloalkyl group, and a $Si(C_{1-40}$ alkyl$)_3$ group.

13. A thin film semiconductor comprising a compound of claim 1.

14. A composite comprising a substrate and the thin film semiconductor of claim 13 deposited on the substrate.

15. An electronic device, an optical device, or an optoelectronic device comprising the thin film semiconductor of claim 13.

16. An electronic device, an optical device, or an optoelectronic device comprising the composite of claim 14.

17. A field effect transistor device comprising a source electrode, a drain electrode, a gate electrode, and the thin film semiconductor of claim 13 in contact with a dielectric material.

18. The field effect transistor device of claim 17, wherein the field effect transistor has a structure selected from top-gate bottom-contact structure, bottom-gate top-contact structure, top-gate top-contact structure, and bottom-gate bottom-contact structure.

19. The field effect transistor device of claim 18, wherein the dielectric material comprises an organic dielectric material.

20. The field effect transistor device of claim 18, wherein the dielectric material comprises an inorganic dielectric material or a hybrid organic/inorganic dielectric material.

* * * * *